(12) United States Patent
Hanada et al.

(10) Patent No.: US 10,450,372 B2
(45) Date of Patent: Oct. 22, 2019

(54) ANTI-THYROGLOBULIN T CELL RECEPTORS

(71) Applicant: The United States of America, as represented by the Secretary, Department of Health and Human Services, Bethesda, MD (US)

(72) Inventors: Kenichi Hanada, Bethesda, MD (US); Qiong J. Wang, Potomac, MD (US); James C. Yang, Bethesda, MD (US); Zhiya Yu, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 51 days.

(21) Appl. No.: 15/524,869

(22) PCT Filed: Nov. 12, 2015

(86) PCT No.: PCT/US2015/060282
§ 371 (c)(1),
(2) Date: May 5, 2017

(87) PCT Pub. No.: WO2016/077525
PCT Pub. Date: May 19, 2016

(65) Prior Publication Data
US 2018/0244768 A1    Aug. 30, 2018

Related U.S. Application Data

(60) Provisional application No. 62/079,713, filed on Nov. 14, 2014.

(51) Int. Cl.
*C07K 16/26* (2006.01)
*C07K 14/725* (2006.01)
*A61P 35/04* (2006.01)
*A61P 35/00* (2006.01)
*A61K 38/00* (2006.01)

(52) U.S. Cl.
CPC ............. *C07K 16/26* (2013.01); *A61P 35/00* (2018.01); *A61P 35/04* (2018.01); *C07K 14/7051* (2013.01); *A61K 38/00* (2013.01); *C07K 2317/34* (2013.01); *C07K 2317/565* (2013.01); *C07K 2318/20* (2013.01); *C07K 2319/00* (2013.01)

(58) Field of Classification Search
CPC ............ C07K 14/7051; C07K 2317/34; C07K 2318/20; C07K 2317/565
USPC .......................................... 424/133.1, 134.1
See application file for complete search history.

(56) References Cited

U.S. PATENT DOCUMENTS

| 4,874,845 | A  | 10/1989 | Saito et al. |
| 8,034,334 | B2 | 10/2011 | Dudley et al. |
| 8,383,099 | B2 | 2/2013  | Dudley et al. |
| 2012/0244133 | A1 | 9/2012 | Rosenberg et al. |

FOREIGN PATENT DOCUMENTS

| WO | WO 2012/166617 A2 | 12/2012 |
| WO | WO 2015/150327 A1 | 10/2015 |

OTHER PUBLICATIONS

Baird et al., "Gene Engineered T-cells for the Immunotherapy of Differentiated Thyroid Cancer," poster presented at the Endocrine Society 94th Annual Meeting, (Jun. 23-26, 2012).
Baird, "Gene Engineered T-cells for the Immunotherapy of Differentiated Thyroid Cancer," Thesis, Duke University School of Medicine (2012).
Cohen et al., "Enhanced antitumor activity of murine-human hybrid T-cell receptor (TCR) in human lymphocytes is associated with improved pairing and TCR/CD3 stability," *Cancer Res.*, 66(17): 8878-86 (2006).
Davies et al., "Current Thyroid Cancer Trends in the United States," *JAMA Otolaryngol Head Neck Surg.*, 140(4):317-322 (2014).
Dudley et al., "Generation of Tumor-Infiltrating Lymphocyte Cultures for Use in Adoptive Transfer Therapy for Melanoma Patients," *J Immunother.*, 26(4): 332-342 (2003).
Ehlers et al., "Evidence of a Combined Cytotoxic Thyroglobulin and Thyroperoxidase Epitope-Specific Cellular Immunity in Hashimoto's Thyroiditis," *J Clin Endocrinol Metab*, 97: 1347-1354 (2012).
International Bureau, International Search Report in International Application No. PCT/US2015/060282, dated Nov. 21, 2016.
International Bureau, Written Opinion in International Application No. PCT/US2015/060282, dated Nov. 21, 2016.
Jiang et al., "Variable influences of iodine on the T-cell recognition of a single thyroglobulin epitope," *Immunology*, 121: 370-376 (2007).
Kloos, "Approach to the patient with a positive serum thyroglobulin and a negative radioiodine scan after initial therapy for differentiated thyroid cancer," *J. Clin. Endocrinol. Metab.*, 93(5): 1519-1525 (2008).
Kochenderfer et al., "B-cell depletion and remissions of malignancy along with cytokine-associated toxicity in a clinical trial of anti-CD19 chimeric-antigen-receptor-transduced T cells," *Blood*, 119(12): 2709-2720 (2012).
Matsuoka et al., "Thyroglobulin-Induced Murine Thyroiditis Assessed by Intrathyroidal T Cell Receptor Sequencing," *J. Immunol.*, 152(5): 2562-68 (1994).

(Continued)

*Primary Examiner* — Lynn A Bristol
(74) *Attorney, Agent, or Firm* — Leydig, Voit & Mayer, Ltd.

(57) ABSTRACT

Disclosed is a synthetic T cell receptor (TCR) having antigenic specificity for an HLA-A2-restricted epitope of thyroglobulin (TG), $TG_{470-478}$. Related polypeptides and proteins, as well as related nucleic acids, recombinant expression vectors, host cells, and populations of cells are also provided. Antibodies, or an antigen binding portion thereof, and pharmaceutical compositions relating to the TCRs of the disclosure are also provided. Also disclosed are methods of detecting the presence of cancer in a mammal and methods of treating or preventing cancer in a mammal.

27 Claims, 3 Drawing Sheets

Specification includes a Sequence Listing.

(56) References Cited

OTHER PUBLICATIONS

Nakashima et al., "The role of T cells expressing TcR V beta 13 in autoimmune thyroiditis induced by transfer of mouse thyroglobulin-activated lymphocytes: identification of two common CDR3 motifs," *Clin. Immunol. and Immunopathol.*, 80(2): 204-210 (1996).

Rao et al., "Recruitment of multiple V beta genes in the TCR repertoire against a single pathogenic thyroglobulin epitope," *Immunology*, 91: 623-27 (1997).

Riddell et al., "The use of anti-CD3 and anti-CD28 monoclonal antibodies to clone and expand human antigen-specific T cells," *Journal of Immunological Methods*, 128: 189-201 (1990).

Robbins et al., "Tumor regression in patients with metastatic synovial cell sarcoma and melanoma using genetically engineered lymphocytes reactive with NY-ESO-1," *J. Clin. Oncol.*, 29(7): 917-24 (2011).

Stetson et al., "Constitutive Cytokine mRNAs Mark Natural Killer (NK) and NK T Cells Poised for Rapid Effector Function," *The Journal of Experimental Medicine*, 198 (7) : 1069-76 (2003).

Topalian et al., "Tumor-specific cytolysis by lymphocytes infiltrating human melanomas," *The Journal of Immunology*, 142(10): 3714-25 (1989).

Van Staveren et al., "Human Thyroid Tumor Cell Lines Derived from Different Tumor Types Present a Common Dedifferentiated Phenotype," *Cancer Research*, 67(17): 8113-20 (2007).

Wang et al., "Development of a genetically-modified novel T-cell receptor for adoptive cell transfer against renal cell carcinoma," *J. Immunol. Methods*, 366(1-2): 43-51 (2011).

Zhao et al., "Primary Human Lymphocytes Transduced with NY-ESO-1 Antigen-Specific TCR Genes Recognize and Kill Diverse Human Tumor Cell Lines," *J. Immunol.*, 174(7): 4415-23 (2005).

SEQUENCE LISTING

```
<160> NUMBER OF SEQ ID NOS: 58

<210> SEQ ID NO 1
<211> LENGTH: 2768
<212> TYPE: PRT
<213> ORGANISM: Homo sapiens

<400> SEQUENCE: 1

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95
```

```
Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
            115                 120                 125

Val Gln Cys Asp Val Gln Val Gln Cys Trp Cys Val Asp Ala Glu
130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
            195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270

Glu Thr Thr Leu Tyr Arg Ile Leu Gln Arg Arg Phe Leu Ala Val Gln
            275                 280                 285

Ser Val Ile Ser Gly Arg Phe Arg Cys Pro Thr Lys Cys Glu Val Glu
            290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
            340                 345                 350

Gly Glu Pro Pro Ser Cys Ala Glu Gly Gln Ser Cys Ala Ser Glu Arg
            355                 360                 365

Gln Gln Ala Leu Ser Arg Leu Tyr Phe Gly Thr Ser Gly Tyr Phe Ser
    370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
            435                 440                 445

Pro Ser Arg Gly Leu Ala Arg Leu Ala Leu Gln Phe Thr Thr Asn Pro
            450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Phe Gln Leu Gly Leu Ala Ser Phe Leu Asn Gly
            500                 505                 510
```

-continued

Gly Arg Gln Glu Asp Leu Ala Lys Pro Leu Ser Val Gly Leu Asp Ser
                515                 520                 525

Asn Ser Ser Thr Gly Thr Pro Glu Ala Ala Lys Lys Asp Gly Thr Met
530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
                565                 570                 575

Phe Leu Leu Phe Leu Gln His Ala Ile Ser Val Pro Glu Asp Val Ala
                580                 585                 590

Arg Asp Leu Gly Asp Val Met Glu Thr Val Leu Ser Ser Gln Thr Cys
                595                 600                 605

Glu Gln Thr Pro Glu Arg Leu Phe Val Pro Ser Cys Thr Thr Glu Gly
                610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
                645                 650                 655

Arg Cys Pro Thr Asp Cys Glu Lys Gln Arg Ala Arg Met Gln Ser Leu
                660                 665                 670

Met Gly Ser Gln Pro Ala Gly Ser Thr Leu Phe Val Pro Ala Cys Thr
                675                 680                 685

Ser Glu Gly His Phe Leu Pro Val Gln Cys Phe Asn Ser Glu Cys Tyr
                690                 695                 700

Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
                740                 745                 750

Pro Thr Leu Ser Asp Thr Tyr Ile Pro Gln Cys Ser Thr Asp Gly Gln
                755                 760                 765

Trp Arg Gln Val Gln Cys Asn Gly Pro Pro Glu Gln Val Phe Glu Leu
770                 775                 780

Tyr Gln Arg Trp Glu Ala Gln Asn Lys Gly Gln Asp Leu Thr Pro Ala
785                 790                 795                 800

Lys Leu Leu Val Lys Ile Met Ser Tyr Arg Glu Ala Ala Ser Gly Asn
                805                 810                 815

Phe Ser Leu Phe Ile Gln Ser Leu Tyr Glu Ala Gly Gln Gln Asp Val
                820                 825                 830

Phe Pro Val Leu Ser Gln Tyr Pro Ser Leu Gln Asp Val Pro Leu Ala
                835                 840                 845

Ala Leu Glu Gly Lys Arg Pro Gln Pro Arg Glu Asn Ile Leu Leu Glu
850                 855                 860

Pro Tyr Leu Phe Trp Gln Ile Leu Asn Gly Gln Leu Ser Gln Tyr Pro
865                 870                 875                 880

Gly Ser Tyr Ser Asp Phe Ser Thr Pro Leu Ala His Phe Asp Leu Arg
                885                 890                 895

Asn Cys Trp Cys Val Asp Glu Ala Gly Gln Glu Leu Glu Gly Met Arg
                900                 905                 910

Ser Glu Pro Ser Lys Leu Pro Thr Cys Pro Gly Ser Cys Glu Glu Ala
                915                 920                 925

Lys Leu Arg Val Leu Gln Phe Ile Arg Glu Thr Glu Glu Ile Val Ser

-continued

```
                930             935             940
Ala Ser Asn Ser Ser Arg Phe Pro Leu Gly Glu Ser Phe Leu Val Ala
945             950             955             960

Lys Gly Ile Arg Leu Arg Asn Glu Asp Leu Gly Leu Pro Pro Leu Phe
                965             970             975

Pro Pro Arg Glu Ala Phe Ala Glu Gln Phe Leu Arg Gly Ser Asp Tyr
            980             985             990

Ala Ile Arg Leu Ala Ala Gln Ser Thr Leu Ser Phe Tyr Gln Arg Arg
        995             1000            1005

Arg Phe Ser Pro Asp Asp Ser Ala Gly Ala Ser Ala Leu Leu Arg
    1010            1015            1020

Ser Gly Pro Tyr Met Pro Gln Cys Asp Ala Phe Gly Ser Trp Glu
    1025            1030            1035

Pro Val Gln Cys His Ala Gly Thr Gly His Cys Trp Cys Val Asp
    1040            1045            1050

Glu Lys Gly Gly Phe Ile Pro Gly Ser Leu Thr Ala Arg Ser Leu
    1055            1060            1065

Gln Ile Pro Gln Cys Pro Thr Thr Cys Glu Lys Ser Arg Thr Ser
    1070            1075            1080

Gly Leu Leu Ser Ser Trp Lys Gln Ala Arg Ser Gln Glu Asn Pro
    1085            1090            1095

Ser Pro Lys Asp Leu Phe Val Pro Ala Cys Leu Glu Thr Gly Glu
    1100            1105            1110

Tyr Ala Arg Leu Gln Ala Ser Gly Ala Gly Thr Trp Cys Val Asp
    1115            1120            1125

Pro Ala Ser Gly Glu Glu Leu Arg Pro Gly Ser Ser Ser Ala
    1130            1135            1140

Gln Cys Pro Ser Leu Cys Asn Val Leu Lys Ser Gly Val Leu Ser
    1145            1150            1155

Arg Arg Val Ser Pro Gly Tyr Val Pro Ala Cys Arg Ala Glu Asp
    1160            1165            1170

Gly Gly Phe Ser Pro Val Gln Cys Asp Gln Ala Gln Gly Ser Cys
    1175            1180            1185

Trp Cys Val Met Asp Ser Gly Glu Glu Val Pro Gly Thr Arg Val
    1190            1195            1200

Thr Gly Gly Gln Pro Ala Cys Glu Ser Pro Arg Cys Pro Leu Pro
    1205            1210            1215

Phe Asn Ala Ser Glu Val Val Gly Gly Thr Ile Leu Cys Glu Thr
    1220            1225            1230

Ile Ser Gly Pro Thr Gly Ser Ala Met Gln Gln Cys Gln Leu Leu
    1235            1240            1245

Cys Arg Gln Gly Ser Trp Ser Val Phe Pro Pro Gly Pro Leu Ile
    1250            1255            1260

Cys Ser Leu Glu Ser Gly Arg Trp Glu Ser Gln Leu Pro Gln Pro
    1265            1270            1275

Arg Ala Cys Gln Arg Pro Gln Leu Trp Gln Thr Ile Gln Thr Gln
    1280            1285            1290

Gly His Phe Gln Leu Gln Leu Pro Pro Gly Lys Met Cys Ser Ala
    1295            1300            1305

Asp Tyr Ala Asp Leu Leu Gln Thr Phe Gln Val Phe Ile Leu Asp
    1310            1315            1320

Glu Leu Thr Ala Arg Gly Phe Cys Gln Ile Gln Val Lys Thr Phe
    1325            1330            1335
```

-continued

```
Gly Thr Leu Val Ser Ile Pro Val Cys Asn Asn Ser Ser Val Gln
    1340                1345                1350

Val Gly Cys Leu Thr Arg Glu Arg Leu Gly Val Asn Val Thr Trp
    1355                1360                1365

Lys Ser Arg Leu Glu Asp Ile Pro Val Ala Ser Leu Pro Asp Leu
    1370                1375                1380

His Asp Ile Glu Arg Ala Leu Val Gly Lys Asp Leu Leu Gly Arg
    1385                1390                1395

Phe Thr Asp Leu Ile Gln Ser Gly Ser Phe Gln Leu His Leu Asp
    1400                1405                1410

Ser Lys Thr Phe Pro Ala Glu Thr Ile Arg Phe Leu Gln Gly Asp
    1415                1420                1425

His Phe Gly Thr Ser Pro Arg Thr Trp Phe Gly Cys Ser Glu Gly
    1430                1435                1440

Phe Tyr Gln Val Leu Thr Ser Glu Ala Ser Gln Asp Gly Leu Gly
    1445                1450                1455

Cys Val Lys Cys Pro Glu Gly Ser Tyr Ser Gln Asp Glu Glu Cys
    1460                1465                1470

Ile Pro Cys Pro Val Gly Phe Tyr Gln Glu Gln Ala Gly Ser Leu
    1475                1480                1485

Ala Cys Val Pro Cys Pro Val Gly Arg Thr Thr Ile Ser Ala Gly
    1490                1495                1500

Ala Phe Ser Gln Thr His Cys Val Thr Asp Cys Gln Arg Asn Glu
    1505                1510                1515

Ala Gly Leu Gln Cys Asp Gln Asn Gly Gln Tyr Arg Ala Ser Gln
    1520                1525                1530

Lys Asp Arg Gly Ser Gly Lys Ala Phe Cys Val Asp Gly Glu Gly
    1535                1540                1545

Arg Arg Leu Pro Trp Trp Glu Thr Glu Ala Pro Leu Glu Asp Ser
    1550                1555                1560

Gln Cys Leu Met Met Gln Lys Phe Glu Lys Val Pro Glu Ser Lys
    1565                1570                1575

Val Ile Phe Asp Ala Asn Ala Pro Val Ala Val Arg Ser Lys Val
    1580                1585                1590

Pro Asp Ser Glu Phe Pro Val Met Gln Cys Leu Thr Asp Cys Thr
    1595                1600                1605

Glu Asp Glu Ala Cys Ser Phe Phe Thr Val Ser Thr Thr Glu Pro
    1610                1615                1620

Glu Ile Ser Cys Asp Phe Tyr Ala Trp Thr Ser Asp Asn Val Ala
    1625                1630                1635

Cys Met Thr Ser Asp Gln Lys Arg Asp Ala Leu Gly Asn Ser Lys
    1640                1645                1650

Ala Thr Ser Phe Gly Ser Leu Arg Cys Gln Val Lys Val Arg Ser
    1655                1660                1665

His Gly Gln Asp Ser Pro Ala Val Tyr Leu Lys Lys Gly Gln Gly
    1670                1675                1680

Ser Thr Thr Thr Leu Gln Lys Arg Phe Glu Pro Thr Gly Phe Gln
    1685                1690                1695

Asn Met Leu Ser Gly Leu Tyr Asn Pro Ile Val Phe Ser Ala Ser
    1700                1705                1710

Gly Ala Asn Leu Thr Asp Ala His Leu Phe Cys Leu Leu Ala Cys
    1715                1720                1725
```

-continued

Asp Arg Asp Leu Cys Cys Asp Gly Phe Val Leu Thr Gln Val Gln
1730                1735                1740

Gly Gly Ala Ile Ile Cys Gly Leu Leu Ser Ser Pro Ser Val Leu
1745                1750                1755

Leu Cys Asn Val Lys Asp Trp Met Asp Pro Ser Glu Ala Trp Ala
1760                1765                1770

Asn Ala Thr Cys Pro Gly Val Thr Tyr Asp Gln Glu Ser His Gln
1775                1780                1785

Val Ile Leu Arg Leu Gly Asp Gln Glu Phe Ile Lys Ser Leu Thr
1790                1795                1800

Pro Leu Glu Gly Thr Gln Asp Thr Phe Thr Asn Phe Gln Gln Val
1805                1810                1815

Tyr Leu Trp Lys Asp Ser Asp Met Gly Ser Arg Pro Glu Ser Met
1820                1825                1830

Gly Cys Arg Lys Asp Thr Val Pro Arg Pro Ala Ser Pro Thr Glu
1835                1840                1845

Ala Gly Leu Thr Thr Glu Leu Phe Ser Pro Val Asp Leu Asn Gln
1850                1855                1860

Val Ile Val Asn Gly Asn Gln Ser Leu Ser Ser Gln Lys His Trp
1865                1870                1875

Leu Phe Lys His Leu Phe Ser Ala Gln Gln Ala Asn Leu Trp Cys
1880                1885                1890

Leu Ser Arg Cys Val Gln Glu His Ser Phe Cys Gln Leu Ala Glu
1895                1900                1905

Ile Thr Glu Ser Ala Ser Leu Tyr Phe Thr Cys Thr Leu Tyr Pro
1910                1915                1920

Glu Ala Gln Val Cys Asp Asp Ile Met Glu Ser Asn Ala Gln Gly
1925                1930                1935

Cys Arg Leu Ile Leu Pro Gln Met Pro Lys Ala Leu Phe Arg Lys
1940                1945                1950

Lys Val Ile Leu Glu Asp Lys Val Lys Asn Phe Tyr Thr Arg Leu
1955                1960                1965

Pro Phe Gln Lys Leu Met Gly Ile Ser Ile Arg Asn Lys Val Pro
1970                1975                1980

Met Ser Glu Lys Ser Ile Ser Asn Gly Phe Phe Glu Cys Glu Arg
1985                1990                1995

Arg Cys Asp Ala Asp Pro Cys Cys Thr Gly Phe Gly Phe Leu Asn
2000                2005                2010

Val Ser Gln Leu Lys Gly Gly Glu Val Thr Cys Leu Thr Leu Asn
2015                2020                2025

Ser Leu Gly Ile Gln Met Cys Ser Glu Glu Asn Gly Gly Ala Trp
2030                2035                2040

Arg Ile Leu Asp Cys Gly Ser Pro Asp Ile Glu Val His Thr Tyr
2045                2050                2055

Pro Phe Gly Trp Tyr Gln Lys Pro Ile Ala Gln Asn Asn Ala Pro
2060                2065                2070

Ser Phe Cys Pro Leu Val Val Leu Pro Ser Leu Thr Glu Lys Val
2075                2080                2085

Ser Leu Asp Ser Trp Gln Ser Leu Ala Leu Ser Ser Val Val Val
2090                2095                2100

Asp Pro Ser Ile Arg His Phe Asp Val Ala His Val Ser Thr Ala
2105                2110                2115

Ala Thr Ser Asn Phe Ser Ala Val Arg Asp Leu Cys Leu Ser Glu

-continued

```
            2120                2125                2130
Cys Ser Gln His Glu Ala Cys Leu Ile Thr Thr Leu Gln Thr Gln
        2135                2140                2145
Pro Gly Ala Val Arg Cys Met Phe Tyr Ala Asp Thr Gln Ser Cys
        2150                2155                2160
Thr His Ser Leu Gln Gly Gln Asn Cys Arg Leu Leu Leu Arg Glu
        2165                2170                2175
Glu Ala Thr His Ile Tyr Arg Lys Pro Gly Ile Ser Leu Leu Ser
        2180                2185                2190
Tyr Glu Ala Ser Val Pro Ser Val Pro Ile Ser Thr His Gly Arg
        2195                2200                2205
Leu Leu Gly Arg Ser Gln Ala Ile Gln Val Gly Thr Ser Trp Lys
        2210                2215                2220
Gln Val Asp Gln Phe Leu Gly Val Pro Tyr Ala Ala Pro Pro Leu
        2225                2230                2235
Ala Glu Arg Arg Phe Gln Ala Pro Glu Pro Leu Asn Trp Thr Gly
        2240                2245                2250
Ser Trp Asp Ala Ser Lys Pro Arg Ala Ser Cys Trp Gln Pro Gly
        2255                2260                2265
Thr Arg Thr Ser Thr Ser Pro Gly Val Ser Glu Asp Cys Leu Tyr
        2270                2275                2280
Leu Asn Val Phe Ile Pro Gln Asn Val Ala Pro Asn Ala Ser Val
        2285                2290                2295
Leu Val Phe Phe His Asn Thr Met Asp Arg Glu Glu Ser Glu Gly
        2300                2305                2310
Trp Pro Ala Ile Asp Gly Ser Phe Leu Ala Ala Val Gly Asn Leu
        2315                2320                2325
Ile Val Val Thr Ala Ser Tyr Arg Val Gly Val Phe Gly Phe Leu
        2330                2335                2340
Ser Ser Gly Ser Gly Glu Val Ser Gly Asn Trp Gly Leu Leu Asp
        2345                2350                2355
Gln Val Ala Ala Leu Thr Trp Val Gln Thr His Ile Arg Gly Phe
        2360                2365                2370
Gly Gly Asp Pro Arg Arg Val Ser Leu Ala Ala Asp Arg Gly Gly
        2375                2380                2385
Ala Asp Val Ala Ser Ile His Leu Leu Thr Ala Arg Ala Thr Asn
        2390                2395                2400
Ser Gln Leu Phe Arg Arg Ala Val Leu Met Gly Gly Ser Ala Leu
        2405                2410                2415
Ser Pro Ala Ala Val Ile Ser His Glu Arg Ala Gln Gln Gln Ala
        2420                2425                2430
Ile Ala Leu Ala Lys Glu Val Ser Cys Pro Met Ser Ser Ser Gln
        2435                2440                2445
Glu Val Val Ser Cys Leu Arg Gln Lys Pro Ala Asn Val Leu Asn
        2450                2455                2460
Asp Ala Gln Thr Lys Leu Leu Ala Val Ser Gly Pro Phe His Tyr
        2465                2470                2475
Trp Gly Pro Val Ile Asp Gly His Phe Leu Arg Glu Pro Pro Ala
        2480                2485                2490
Arg Ala Leu Lys Arg Ser Leu Trp Val Glu Val Asp Leu Leu Ile
        2495                2500                2505
Gly Ser Ser Gln Asp Asp Gly Leu Ile Asn Arg Ala Lys Ala Val
        2510                2515                2520
```

Lys Gln Phe Glu Glu Ser Arg Gly Arg Thr Ser Ser Lys Thr Ala
            2525                2530                2535

Phe Tyr Gln Ala Leu Gln Asn Ser Leu Gly Gly Glu Asp Ser Asp
        2540                2545                2550

Ala Arg Val Glu Ala Ala Ala Thr Trp Tyr Tyr Ser Leu Glu His
        2555                2560                2565

Ser Thr Asp Asp Tyr Ala Ser Phe Ser Arg Ala Leu Glu Asn Ala
        2570                2575                2580

Thr Arg Asp Tyr Phe Ile Ile Cys Pro Ile Ile Asp Met Ala Ser
        2585                2590                2595

Ala Trp Ala Lys Arg Ala Arg Gly Asn Val Phe Met Tyr His Ala
        2600                2605                2610

Pro Glu Asn Tyr Gly His Gly Ser Leu Glu Leu Leu Ala Asp Val
        2615                2620                2625

Gln Phe Ala Leu Gly Leu Pro Phe Tyr Pro Ala Tyr Glu Gly Gln
        2630                2635                2640

Phe Ser Leu Glu Glu Lys Ser Leu Ser Leu Lys Ile Met Gln Tyr
        2645                2650                2655

Phe Ser His Phe Ile Arg Ser Gly Asn Pro Asn Tyr Pro Tyr Glu
        2660                2665                2670

Phe Ser Arg Lys Val Pro Thr Phe Ala Thr Pro Trp Pro Asp Phe
        2675                2680                2685

Val Pro Arg Ala Gly Gly Glu Asn Tyr Lys Glu Phe Ser Glu Leu
        2690                2695                2700

Leu Pro Asn Arg Gln Gly Leu Lys Lys Ala Asp Cys Ser Phe Trp
        2705                2710                2715

Ser Lys Tyr Ile Ser Ser Leu Lys Thr Ser Ala Asp Gly Ala Lys
        2720                2725                2730

Gly Gly Gln Ser Ala Glu Ser Glu Glu Glu Glu Leu Thr Ala Gly
        2735                2740                2745

Ser Gly Leu Arg Glu Asp Leu Leu Ser Leu Gln Glu Pro Gly Ser
        2750                2755                2760

Lys Thr Tyr Ser Lys
        2765

<210> SEQ ID NO 2
<211> LENGTH: 9
<212> TYPE: PRT
<213> ORGANISM: Homo sapiens

<400> SEQUENCE: 2

Asn Leu Phe Gly Gly Lys Phe Leu Val
1               5

<210> SEQ ID NO 3
<211> LENGTH: 6
<212> TYPE: PRT
<213> ORGANISM: Mus musculus

<400> SEQUENCE: 3

Asp Pro Asn Ser Tyr Tyr
1               5

<210> SEQ ID NO 4
<211> LENGTH: 7
<212> TYPE: PRT
<213> ORGANISM: Mus musculus

<400> SEQUENCE: 4

Val Phe Ser Ser Thr Glu Ile
1               5

<210> SEQ ID NO 5
<211> LENGTH: 11
<212> TYPE: PRT
<213> ORGANISM: Mus musculus

<400> SEQUENCE: 5

Ala Val Ser Ser Gly Ser Trp Gln Leu Ile
1               5                   10

<210> SEQ ID NO 6
<211> LENGTH: 5
<212> TYPE: PRT
<213> ORGANISM: Mus musculus

<400> SEQUENCE: 6

Lys Gly His Pro Val
1               5

<210> SEQ ID NO 7
<211> LENGTH: 6
<212> TYPE: PRT
<213> ORGANISM: Mus musculus

<400> SEQUENCE: 7

Phe Gln Asn Gln Glu Val
1               5

<210> SEQ ID NO 8
<211> LENGTH: 11
<212> TYPE: PRT
<213> ORGANISM: Mus musculus

<400> SEQUENCE: 8

Ala Ser Leu Gly Gly Ser Gln Asp Thr Gln Tyr
1               5                   10

<210> SEQ ID NO 9
<211> LENGTH: 123
<212> TYPE: PRT
<213> ORGANISM: Mus musculus

<400> SEQUENCE: 9

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Ile Cys Thr Tyr Thr Asp
        35                  40                  45

Pro Asn Ser Tyr Tyr Phe Phe Trp Tyr Lys Gln Glu Pro Gly Ala Gly
    50                  55                  60

Leu Gln Leu Leu Met Lys Val Phe Ser Ser Thr Glu Ile Asn Glu Gly
65                  70                  75                  80

Gln Gly Phe Thr Val Leu Leu Asn Lys Lys Asp Lys Gln Leu Ser Leu
                85                  90                  95

Asn Leu Thr Ala Ala His Pro Gly Asp Ser Ala Val Tyr Phe Cys Ala
            100                 105                 110

```
Val Ser Ser Gly Ser Trp Gln Leu Ile Phe
        115                 120

<210> SEQ ID NO 10
<211> LENGTH: 123
<212> TYPE: PRT
<213> ORGANISM: Mus musculus

<400> SEQUENCE: 10

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Glu Phe Lys Phe
    50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Leu Gly Gly Ser Gln Asp Thr Gln Tyr Phe
        115                 120

<210> SEQ ID NO 11
<211> LENGTH: 270
<212> TYPE: PRT
<213> ORGANISM: Mus musculus

<400> SEQUENCE: 11

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Ile Cys Thr Tyr Thr Asp
        35                  40                  45

Pro Asn Ser Tyr Tyr Phe Phe Trp Tyr Lys Gln Glu Pro Gly Ala Gly
    50                  55                  60

Leu Gln Leu Leu Met Lys Val Phe Ser Thr Glu Ile Asn Glu Gly
65                  70                  75                  80

Gln Gly Phe Thr Val Leu Leu Asn Lys Lys Asp Lys Gln Leu Ser Leu
                85                  90                  95

Asn Leu Thr Ala Ala His Pro Gly Asp Ser Ala Val Tyr Phe Cys Ala
            100                 105                 110

Val Ser Ser Gly Ser Trp Gln Leu Ile Phe Gly Ser Gly Thr Gln
        115                 120                 125

Leu Thr Val Met Pro Asp Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190
```

```
Asn Gly Ala Ile Ala Trp Ser Asn Gln Thr Ser Phe Thr Cys Gln Asp
            195                 200                 205

Ile Phe Lys Glu Thr Asn Ala Thr Tyr Pro Ser Ser Asp Val Pro Cys
210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Lys Val
                245                 250                 255

Ala Gly Phe Asn Leu Leu Met Thr Leu Arg Leu Trp Ser Ser
            260                 265                 270

<210> SEQ ID NO 12
<211> LENGTH: 305
<212> TYPE: PRT
<213> ORGANISM: Mus musculus

<400> SEQUENCE: 12

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Asn Glu Phe Lys Phe
    50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Leu Gly Gly Ser Gln Asp Thr Gln Tyr Phe Gly Pro Gly Thr Arg
        115                 120                 125

Leu Leu Val Leu Glu Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300
```

Ser
305

<210> SEQ ID NO 13
<211> LENGTH: 147
<212> TYPE: PRT
<213> ORGANISM: Mus musculus

<400> SEQUENCE: 13

Gly Ser Gly Thr Gln Leu Thr Val Met Pro Asp Ile Gln Asn Pro Glu
1               5                   10                  15

Pro Ala Val Tyr Gln Leu Lys Asp Pro Arg Ser Gln Asp Ser Thr Leu
            20                  25                  30

Cys Leu Phe Thr Asp Phe Asp Ser Gln Ile Asn Val Pro Lys Thr Met
        35                  40                  45

Glu Ser Gly Thr Phe Ile Thr Asp Lys Thr Val Leu Asp Met Lys Ala
50                  55                  60

Met Asp Ser Lys Ser Asn Gly Ala Ile Ala Trp Ser Asn Gln Thr Ser
65                  70                  75                  80

Phe Thr Cys Gln Asp Ile Phe Lys Glu Thr Asn Ala Thr Tyr Pro Ser
                85                  90                  95

Ser Asp Val Pro Cys Asp Ala Thr Leu Thr Glu Lys Ser Phe Glu Thr
            100                 105                 110

Asp Met Asn Leu Asn Phe Gln Asn Leu Ser Val Met Gly Leu Arg Ile
        115                 120                 125

Leu Leu Leu Lys Val Ala Gly Phe Asn Leu Leu Met Thr Leu Arg Leu
130                 135                 140

Trp Ser Ser
145

<210> SEQ ID NO 14
<211> LENGTH: 182
<212> TYPE: PRT
<213> ORGANISM: Mus musculus

<400> SEQUENCE: 14

Gly Pro Gly Thr Arg Leu Leu Val Leu Glu Asp Leu Arg Asn Val Thr
1               5                   10                  15

Pro Pro Lys Val Ser Leu Phe Glu Pro Ser Lys Ala Glu Ile Ala Asn
            20                  25                  30

Lys Gln Lys Ala Thr Leu Val Cys Leu Ala Arg Gly Phe Phe Pro Asp
            35                  40                  45

His Val Glu Leu Ser Trp Trp Val Asn Gly Lys Glu Val His Ser Gly
50                  55                  60

Val Ser Thr Asp Pro Gln Ala Tyr Lys Glu Ser Asn Tyr Ser Tyr Cys
65                  70                  75                  80

Leu Ser Ser Arg Leu Arg Val Ser Ala Thr Phe Trp His Asn Pro Arg
                85                  90                  95

Asn His Phe Arg Cys Gln Val Gln Phe His Gly Leu Ser Glu Glu Asp
            100                 105                 110

Lys Trp Pro Glu Gly Ser Pro Lys Pro Val Thr Gln Asn Ile Ser Ala
        115                 120                 125

Glu Ala Trp Gly Arg Ala Asp Cys Gly Ile Thr Ser Ala Ser Tyr His
130                 135                 140

Gln Gly Val Leu Ser Ala Thr Ile Leu Tyr Glu Ile Leu Leu Gly Lys
145                 150                 155                 160

Ala Thr Leu Tyr Ala Val Leu Val Ser Gly Leu Val Leu Met Ala Met
            165                 170                 175

Val Lys Lys Lys Asn Ser
            180

<210> SEQ ID NO 15
<211> LENGTH: 369
<212> TYPE: DNA
<213> ORGANISM: Mus musculus

<400> SEQUENCE: 15

| | | | | | |
|---|---|---|---|---|---|
| atgaagacag | tgactggacc | tttgttcctg | tgcttctggc | tgcagctgaa | ctgtgtgagc | 60 |
| agaggcgagc | aggtggagca | gcgccctcct | cacctgagtg | tccgggaggg | agacagtgcc | 120 |
| gttatcatct | gcacctacac | agaccctaac | agttattact | tcttctggta | caagcaagag | 180 |
| ccgggggcag | tcttcagtt | gcttatgaag | gttttctcaa | gtacggaaat | aaacgaagga | 240 |
| caaggattca | ctgtcctact | gaacaagaaa | gacaaacaac | tctctctgaa | cctcacagct | 300 |
| gcccatcctg | ggactcagc | cgtgtacttc | tgcgcagtca | gttcttctgg | cagctggcaa | 360 |
| ctcatctttt | | | | | | 369 |

<210> SEQ ID NO 16
<211> LENGTH: 369
<212> TYPE: DNA
<213> ORGANISM: Mus musculus

<400> SEQUENCE: 16

| | | | | | |
|---|---|---|---|---|---|
| atggctacaa | ggctcctctg | ttacacagta | ctttgtctcc | tgggtgcaag | aattttgaat | 60 |
| tcaaaagtca | ttcagactcc | aagatatctg | gtgaaaggc | aaggacaaaa | agcaaagatg | 120 |
| aggtgtatcc | ctgaaaaggg | acatccagtt | gtattctggt | atcaacaaaa | taagaacaat | 180 |
| gagtttaaat | ttttgattaa | cttcagaat | caagaagttc | ttcagcaaat | agacatgact | 240 |
| gaaaaacgat | tctctgctga | gtgtccttca | aactcacctt | gcagcctaga | aattcagtcc | 300 |
| tctgaggcag | gagactcagc | actgtacctc | tgtgccagcc | tggggggaag | ccaagacacc | 360 |
| cagtactttt | | | | | | 369 |

<210> SEQ ID NO 17
<211> LENGTH: 813
<212> TYPE: DNA
<213> ORGANISM: Mus musculus

<400> SEQUENCE: 17

| | | | | | |
|---|---|---|---|---|---|
| atgaagacag | tgactggacc | tttgttcctg | tgcttctggc | tgcagctgaa | ctgtgtgagc | 60 |
| agaggcgagc | aggtggagca | gcgccctcct | cacctgagtg | tccgggaggg | agacagtgcc | 120 |
| gttatcatct | gcacctacac | agaccctaac | agttattact | tcttctggta | caagcaagag | 180 |
| ccgggggcag | tcttcagtt | gcttatgaag | gttttctcaa | gtacggaaat | aaacgaagga | 240 |
| caaggattca | ctgtcctact | gaacaagaaa | gacaaacaac | tctctctgaa | cctcacagct | 300 |
| gcccatcctg | ggactcagc | cgtgtacttc | tgcgcagtca | gttcttctgg | cagctggcaa | 360 |
| ctcatctttg | gatctggaac | ccaactgaca | gttatgcctg | acatccagaa | cccagaacct | 420 |
| gctgtgtacc | agttaaaaga | tcctcggtct | caggacagca | ccctctgcct | gttcaccgac | 480 |
| tttgactccc | aaatcaatgt | gccgaaaacc | atggaatctg | gaacgttcat | cactgacaaa | 540 |
| actgtgctgg | acatgaaagc | tatggattcc | aagagcaatg | gggccattgc | ctggagcaac | 600 |

```
cagacaagct tcacctgcca agatatcttc aaagagacca acgccaccta ccccagttca    660
gacgttccct gtgatgccac gttgactgag aaaagctttg aaacagatat gaacctaaac    720
tttcaaaacc tgtcagttat gggactccga atcctcctgc tgaaagtagc cggatttaac    780
ctgctcatga cgctgaggct gtggtccagt tag                                 813

<210> SEQ ID NO 18
<211> LENGTH: 918
<212> TYPE: DNA
<213> ORGANISM: Mus musculus

<400> SEQUENCE: 18
atggctacaa ggctcctctg ttacacagta ctttgtctcc tgggtgcaag aattttgaat     60
tcaaaagtca ttcagactcc aagatatctg gtgaaagggc aaggacaaaa agcaaagatg    120
aggtgtatcc ctgaaaaggg acatccagtt gtattctggt atcaacaaaa taagaacaat    180
gagtttaaat ttttgattaa ctttcagaat caagaagttc ttcagcaaat agacatgact    240
gaaaaacgat tctctgctga gtgtccttca aactcacctt gcagcctaga aattcagtcc    300
tctgaggcag gagactcagc actgtacctc tgtgccagcc tggggggaag ccaagacacc    360
cagtactttg ggccaggcac tcggctcctc gtgttagagg atctgagaaa tgtgactcca    420
cccaaggtct ccttgtttga gccatcaaaa gcagagattg caaacaaaca aaaggctacc    480
ctcgtgtgct tggccagggg cttcttccct gaccacgtgg agctgagctg gtgggtgaat    540
ggcaaggagg tccacagtgg ggtcagcacg gaccctcagg cctacaagga gcaattat     600 agctactgcc tgagcagccg cctgagggtc tctgctacct tctggcacaa tcctcgaaac    660
cacttccgct gccaagtgca gttccatggg cttcagagg aggacaagtg ccagagggc     720 tcacccaaac ctgtcacaca gaacatcagt gcagaggcct ggggccgagc agactgtgga    780
atcacttcag catcctatca tcaggggggtt ctgtctgcaa ccatcctcta tgagatccta    840
ctggggaagg ccaccctata tgctgtgctg gtcagtggcc tggtgctgat ggccatggtc    900
aagaaaaaaa attcctga                                                 918

<210> SEQ ID NO 19
<211> LENGTH: 441
<212> TYPE: DNA
<213> ORGANISM: Mus musculus

<400> SEQUENCE: 19
ggatctggaa cccaactgac agttatgcct gacatccaga acccagaacc tgctgtgtac     60
cagttaaaag atcctcggtc tcaggacagc accctctgcc tgttcaccga ctttgactcc    120
caaatcaatg tgccgaaaac catggaatct ggaacgttca tcactgacaa aactgtgctg    180
gacatgaaag ctatggatc caagagcaat ggggccattg cctggagcaa ccagacaagc    240
ttcacctgcc aagatatctt caagagacc aacgccaccct accccagttc agacgttccc    300
tgtgatgcca cgttgactga gaaaagctttg gaaacagata tgaacctaaa cttttcaaaac    360 ctgtcagtta tgggactccg aatcctcctg ctgaaagtag ccggatttaa cctgctcatg    420
acgctgaggc tgtggtccag t                                              441

<210> SEQ ID NO 20
<211> LENGTH: 549
<212> TYPE: DNA
<213> ORGANISM: Mus musculus

<400> SEQUENCE: 20
```

```
gggccaggca ctcggctcct cgtgttagag gatctgagaa atgtgactcc acccaaggtc      60
tccttgtttg agccatcaaa agcagagatt gcaaacaaac aaaaggctac cctcgtgtgc     120
ttggccaggg gcttcttccc tgaccacgtg gagctgagct ggtgggtgaa tggcaaggag     180
gtccacagtg gggtcagcac ggaccctcag gcctacaagg agagcaatta tagctactgc     240
ctgagcagcc gcctgagggt ctctgctacc ttctggcaca atcctcgaaa ccacttccgc     300
tgccaagtgc agttccatgg gctttcagag gaggacaagt ggccagaggg ctcacccaaa     360
cctgtcacac agaacatcag tgcagaggcc tggggccgag cagactgtgg aatcacttca     420
gcatcctatc atcaggggt tctgtctgca accatcctct atgagatcct actggggaag     480
gccaccctat atgctgtgct ggtcagtggc ctggtgctga tggccatggt caagaaaaaa     540
aattcctga                                                             549

<210> SEQ ID NO 21
<211> LENGTH: 7394
<212> TYPE: DNA
<213> ORGANISM: Artificial Sequence
<220> FEATURE:
<223> OTHER INFORMATION: Synthetic

<400> SEQUENCE: 21
ccatgaagac agtgactgga cctttgttcc tgtgcttctg gctgcagctg aactgtgtga      60
gcagaggcga gcaggtggag cagcgccctc ctcacctgag tgtccgggag ggagacagtg     120
ccgttatcat ctgcacctac acagacccta acagttatta cttcttctgg tacaagcaag     180 agccggggc aggtcttcag ttgcttatga aggttttctc aagtacggaa ataaacgaag     240
gacaaggatt cactgtccta ctgaacaaga agacaaaaca actctctctg aacctcacag     300
ctgcccatcc tgggactca gccgtgtact tctgcgcagt cagttcttct ggcagctggc     360
aactcatctt tggatctgga acccaactga cagttatgcc tgacatccag aacccagaac     420
ctgctgtgta ccagttaaaa gatcctcggt ctcaggacag caccctctgc ctgttcaccg     480
actttgactc ccaaatcaat gtgccgaaaa ccatggaatc tggaacgttc atcactgaca     540
aaactgtgct ggacatgaaa gctatggatt ccaagagcaa tggggccatt gcctggagca     600
accagacaag cttcacctgc caagatatct tcaaagagac caacgccacc taccccagtt     660
cagacgttcc ctgtgatgcc acgttgactg agaaaagctt tgaaacagat atgaacctaa     720
actttcaaaa cctgtcagtt atgggactcc gaatcctcct gctgaaagta gccggattta     780
acctgctcat gacgctgagg ctgtggtcca gtcgggccaa gcggtccgga tccggagcca     840
ccaacttcag cctgctgaag caggccggcg acgtggagga gaaccccggc cccatggcta     900
caaggctcct ctgttacaca gtactttgtc tcctgggtgc agaattttga aattcaaaag     960
tcattcagac tccaagatat ctggtgaaag ggcaaggaca aaaagcaaag atgaggtgta    1020
tccctgaaaa gggacatcca gttgtattct ggtatcaaca aaataagaac aatgagttta    1080 aattttgat taactttcag aatcaagaag ttcttcagca aatagacatg actgaaaaac    1140
gattctctgc tgagtgtcct tcaaactcac cttgcagcct agaaattcag tcctctgagg    1200
caggagactc agcactgtac ctctgtgcca gcctgggggg aagccaagac acccagtact    1260
ttgggccagg cactcggctc ctcgtgttag aggatctgag aaatgtgact ccacccaagg    1320
tctccttgtt tgagccatca aaagcagaga ttgcaaacaa acaaaaggct accctcgtgt    1380
gcttggccag gggcttcttc cctgaccacg tggagctgag ctggtgggtg aatggcaagg    1440
```

-continued

```
aggtccacag tggggtcagc acggaccctc aggcctacaa ggagagcaat tatagctact      1500
gcctgagcag ccgcctgagg gtctctgcta ccttctggca caatcctcga aaccacttcc      1560
gctgccaagt gcagttccat gggctttcag aggaggacaa gtggccagag ggctcaccca      1620
aacctgtcac acagaacatc agtgcagagg cctggggccg agcagactgt ggaatcactt      1680
cagcatccta tcatcagggg gttctgtctg caaccatcct ctatgagatc ctactgggga      1740
aggccaccct atatgctgtg ctggtcagtg gcctggtgct gatggccatg gtcaagaaaa      1800
aaaattcctg accgaattct gcagtcgacg gtaccgcggg cccgggatcg atccgataaa      1860
ataaaagatt ttatttagtc tccagaaaaa gggggaatg aaagacccca cctgtaggtt      1920
tggcaagcta gcttaagtaa cgccattttg caaggcatgg aaaatacata actgagaata      1980
gagaagttca gatcaaggtt aggaacagag agacagcaga atatgggcca aacaggatat      2040
ctgtggtaag cagttcctgc cccggctcag ggccaagaac agatggtccc cagatgcggt      2100
cccgccctca gcagtttcta gagaaccatc agatgtttcc agggtgcccc aaggacctga      2160
aaatgaccct gtgccttatt tgaactaacc aatcagttcg cttctcgctt ctgttcgcgc      2220
gcttctgctc cccgagctca ataaaagagc ccacaacccc tcactcggcg cgccagtcct      2280
ccgatagact gcgtcgcccg ggtacccgtg tatccaataa accctcttgc agttgcatcc      2340
gacttgtggt ctcgctgttc cttgggaggg tctcctctga gtgattgact acccgtcagc      2400
gggggtcttt catgggtaac agtttcttga agttggagaa caacattctg agggtaggag      2460
tcgaatatta agtaatcctg actcaattag ccactgtttt gaatccacat actccaatac      2520
tcctgaaatc catcgatgga gttcattatg gacagcgcag aaagagctgg ggagaattgt      2580
gaaattgtta tccgctcaca attccacaca acatacgagc cggaagcata aagtgtaaag      2640
cctggggtgc ctaatgagtg agctaactca cattaattgc gttgcgctca ctgcccgctt      2700
tccagtcggg aaacctgtcg tgccagctgc attaatgaat cggccaacgc gcggggagag      2760
gcggtttgcg tattgggcgc tcttccgctt cctcgctcac tgactcgctg cgctcggtcg      2820
ttcggctgcg gcgagcggta tcagctcact caaaggcggt aatacggtta tccacagaat      2880
caggggataa cgcaggaaag aacatgtgag caaaaggcca gcaaaaggcc aggaaccgta      2940
aaaaggccgc gttgctggcg tttttccata ggctccgccc ccctgacgag catcacaaaa      3000
atcgacgctc aagtcagagg tggcgaaacc cgacaggact ataaagatac caggcgtttc      3060
cccctggaag ctccctcgtg cgctctcctg ttccgaccct gccgcttacc ggatacctgt      3120
ccgcctttct cccttcggga agcgtggcgc tttctcatag ctcacgctgt aggtatctca      3180
gttcggtgta ggtcgttcgc tccaagctgg gctgtgtgca cgaaccccc gttcagcccg      3240 accgctgcgc cttatccggt aactatcgtc ttgagtccaa cccggtaaga cacgacttat      3300
cgccactggc agcagccact ggtaacagga ttagcagagc gaggtatgta ggcggtgcta      3360
cagagttctt gaagtggtgg cctaactacg gctacactag aaggacagta tttggtatct      3420
gcgctctgct gaagccagtt accttcggaa aaagagttgg tagctcttga tccggcaaac      3480
aaaccaccgc tggtagcggt ggtttttttg tttgcaagca gcagattacg cgcagaaaaa      3540
aaggatctca agaagatcct ttgatctttt ctacggggtc tgacgctcag tggaacgaaa      3600
actcacgtta agggattttg gtcatgagat tatcaaaaag gatcttcacc tagatccttt      3660
taaattaaaa atgaagtttt aaatcaatct aaagtatata tgagtaaact tggtctgaca      3720
gttaccaatg cttaatcagt gaggcaccta tctcagcgat ctgtctattt cgttcatcca      3780
tagttgcctg actccccgtc gtgtagataa ctacgatacg ggagggctta ccatctggcc      3840
```

```
ccagtgctgc aatgataccg cgagacccac gctcaccggc tccagattta tcagcaataa   3900
accagccagc cggaagggcc gagcgcagaa gtggtcctgc aactttatcc gcctccatcc   3960
agtctattaa ttgttgccgg gaagctagag taagtagttc gccagttaat agtttgcgca   4020
acgttgttgc cattgctaca ggcatcgtgg tgtcacgctc gtcgtttggt atggcttcat   4080
tcagctccgg ttcccaacga tcaaggcgag ttacatgatc ccccatgttg tgcaaaaaag   4140
cggttagctc cttcggtcct ccgatcgttg tcagaagtaa gttggccgca gtgttatcac   4200
tcatggttat ggcagcactg cataattctc ttactgtcat gccatccgta agatgctttt   4260
ctgtgactgg tgagtactca accaagtcat tctgagaata gtgtatgcgg cgaccgagtt   4320
gctcttgccc ggcgtcaata cgggataata ccgcgccaca tagcagaact ttaaaagtgc   4380
tcatcattgg aaaacgttct cggggcgaaa actctcaag gatcttaccg ctgttgagat   4440
ccagttcgat gtaacccact cgtgcaccca actgatcttc agcatctttt actttcacca   4500
gcgtttctgg gtgagcaaaa acaggaaggc aaaatgccgc aaaaaaggga ataagggcga   4560
cacggaaatg ttgaatactc atactcttcc tttttcaata ttattgaagc atttatcagg   4620
gttattgtct catgagcgga tacatatttg aatgtattta aaaaataaa caaatagggg   4680 ttccgcgcac atttccccga aaagtgccac ctgacgtcta agaaaccatt attatcatga   4740
cattaaccta taaaaatagg cgtatcacga ggccctttcg tctcgcgcgt ttcggtgatg   4800
acggtgaaaa cctctgacac atgcagctcc cggagacggt cacagcttgt ctgtaagcgg   4860
atgccgggag cagacaagcc cgtcaggcg cgtcagcggg tgttggcggg tgtcggggct   4920
ggcttaacta tgcggcatca gagcagattg tactgagagt gcaccatatg cggtgtgaaa   4980
taccgcacag atgcgtaagg agaaaatacc gcatcaggcg ccattcgcca ttcaggctgc   5040
gcaactgttg ggaagggcga tcggtgcggg cctcttcgct attacgccag ctggcgaaag   5100
ggggatgtgc tgcaaggcga ttaagttggg taacgccagg gttttcccag tcacgacgtt   5160
gtaaaacgac ggccagtgcc acgctctccc ttatgcgact cctgcattag gaagcagccc   5220
agtagtaggt tgaggccgtt gagcaccgcc gccgcaagga atggtgcatg caaggagatg   5280
gcgcccaaca gtcccccggc cacggggcct gccaccatac ccacgccgaa acaagcgctc   5340
atgagcccga gtggcgagc ccgatcttcc ccatcggtga tgtcggcgat ataggcgcca   5400
gcaaccgcac ctgtggcgcc ggtgatgccg gccacgatgc gtccggcgta gaggcgattt   5460
aaagacagga tatcagtggt ccaggctcta gttttgactc aacaatatca ccagctgaag   5520
cctatagagt acgagccata gataaaataa aagattttat ttagtctcca gaaaagggg   5580 ggaatgaaag accccacctg taggtttggc aagctagctt aagtaacgcc attttgcaag   5640
gcatggaaaa tacataactg agaatagaga agttcagatc aaggttagga acagagagac   5700
agcagaatat gggccaaaca ggatatctgt ggtaagcagt tcctgccccg gctcagggcc   5760
aagaacagat ggtccccaga tgcggtcccg ccctcagcag tttctagaga accatcagat   5820
gtttccaggg tgccccaagg acctgaaaat gaccctgtgc cttatttgaa ctaaccaatc   5880
agttcgcttc tcgcttctgt tcgcgcgctt ctgctcccg agctcaataa aagagcccac   5940
aacccctcac tcggcgcgcc agtcctccga tagactgcgt cgcccgggta cccgtattcc   6000
caataaagcc tcttgctgtt tgcatccgaa tcgtggactc gctgatcctt gggagggtct   6060
cctcagattg attgactgcc cacctcgggg gtctttcatt tggaggttcc accgagattt   6120
ggagacccct gcctagggac caccgacccc ccgccgggga ggtaagctgg ccagcggtcg   6180
```

-continued

```
tttcgtgtct gtctctgtct ttgtgcgtgt ttgtgccggc atctaatgtt tgcgcctgcg    6240
tctgtactag ttagctaact agctctgtat ctggcggacc cgtggtggaa ctgacgagtt    6300
cggaacaccc ggccgcaacc ctgggagacg tcccagggac ttcggggggcc gttttttgtgg  6360 cccgacctga gtccaaaaat cccgatcgtt ttggactctt tggtgcaccc cccttagagg    6420
agggatatgt ggttctggta ggagacgaga acctaaaaca gttcccgcct ccgtctgaat    6480
ttttgctttc ggtttgggac cgaagccgcg ccgcgcgtct tgtctgctgc agcatcgttc    6540
tgtgttgtct ctgtctgact gtgtttctgt atttgtctga gaatatgggc ccgggctagc    6600
ctgttaccac tcccttaagt ttgacccttag gtcactggaa agatgtcgag cggatcgctc    6660
acaaccagtc ggtagatgtc aagaagagac gttgggttac cttctgctct gcagaatggc    6720
caacctttaa cgtcggatgg ccgcgagacg gcacctttaa ccgagacctc atcacccagg    6780
ttaagatcaa ggtcttttca cctggcccgc atggacaccc agaccaggtc ccctacatcg    6840
tgacctggga agccttggct tttgaccccc ctccctgggt caagccctt gtacacccta    6900 agcctccgcc tcctcttcct ccatccgccc cgtctctccc ccttgaacct cctcgttcga    6960
ccccgcctcg atcctccctt tatccagccc tcactccttc tctaggcgcc cccatatggc    7020
catatgagat cttatatggg gcaccccgc cccttgtaaa cttccctgac cctgacatga     7080
caagagttac taacagcccc tctctccaag ctcacttaca ggctctctac ttagtccagc    7140
acgaagtctg gagacctctg gcggcagcct accaagaaca actggaccga ccggtggtac    7200 ctcacccctta ccgagtcggc gacacagtgt gggtccgccg acaccagact aagaacctag    7260
aacctcgctg gaaaggacct tacacagtcc tgctgaccac ccccaccgcc ctcaaagtag    7320
acggcatcgc agcttggata cacgccgccc acgtgaaggc tgccgacccc gggggtggac    7380
catcctctag accg                                                      7394
```

<210> SEQ ID NO 22
<211> LENGTH: 18
<212> TYPE: DNA
<213> ORGANISM: Mus musculus

<400> SEQUENCE: 22
gaccctaaca gttattac    18

<210> SEQ ID NO 23
<211> LENGTH: 21
<212> TYPE: DNA
<213> ORGANISM: Mus musculus

<400> SEQUENCE: 23
gttttctcaa gtacggaaat a    21

<210> SEQ ID NO 24
<211> LENGTH: 33
<212> TYPE: DNA
<213> ORGANISM: Mus musculus

<400> SEQUENCE: 24
gcagtcagtt cttctggcag ctggcaactc atc    33

<210> SEQ ID NO 25
<211> LENGTH: 15
<212> TYPE: DNA
<213> ORGANISM: Mus musculus

<400> SEQUENCE: 25
aagggacatc cagtt                                              15

<210> SEQ ID NO 26
<211> LENGTH: 18
<212> TYPE: DNA
<213> ORGANISM: Mus musculus

<400> SEQUENCE: 26
tttcagaatc aagaagtt                                           18

<210> SEQ ID NO 27
<211> LENGTH: 33
<212> TYPE: DNA
<213> ORGANISM: Mus musculus

<400> SEQUENCE: 27
gccagcctgg ggggaagcca agacacccag tac                          33

<210> SEQ ID NO 28
<211> LENGTH: 27
<212> TYPE: PRT
<213> ORGANISM: Artificial Sequence
<220> FEATURE:
<223> OTHER INFORMATION: Synthetic

<400> SEQUENCE: 28

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 29
<211> LENGTH: 9
<212> TYPE: PRT
<213> ORGANISM: Homo sapiens

<400> SEQUENCE: 29

Thr Leu Leu Ala Ser Ile Cys Trp Val
1               5

<210> SEQ ID NO 30
<211> LENGTH: 9
<212> TYPE: PRT
<213> ORGANISM: Homo sapiens

<400> SEQUENCE: 30

Glu Leu Pro Glu Phe Leu Leu Phe Leu
1               5

<210> SEQ ID NO 31
<211> LENGTH: 9
<212> TYPE: PRT
<213> ORGANISM: Homo sapiens

<400> SEQUENCE: 31

Ala Leu Val Leu Glu Ile Phe Thr Leu
1               5

<210> SEQ ID NO 32
<211> LENGTH: 9
<212> TYPE: PRT
<213> ORGANISM: Homo sapiens

<400> SEQUENCE: 32

```
Ile Leu Gln Arg Arg Phe Leu Ala Val
1               5

<210> SEQ ID NO 33
<211> LENGTH: 9
<212> TYPE: PRT
<213> ORGANISM: Homo sapiens

<400> SEQUENCE: 33

Ala Leu Leu Arg Ser Gly Pro Tyr Met
1               5

<210> SEQ ID NO 34
<211> LENGTH: 8
<212> TYPE: PRT
<213> ORGANISM: Homo sapiens

<400> SEQUENCE: 34

Leu Val Glu Ile Phe Thr Leu Leu
1               5

<210> SEQ ID NO 35
<211> LENGTH: 9
<212> TYPE: PRT
<213> ORGANISM: Homo sapiens

<400> SEQUENCE: 35

Val Gln Gln Val Gln Cys Trp Cys Val
1               5

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
ggctactttc agcaggagga                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
aggcctctgc actgatgttc                                          20

<210> SEQ ID NO 38
<211> LENGTH: 41
<212> TYPE: DNA
<213> ORGANISM: Artificial Sequence
<220> FEATURE:
<223> OTHER INFORMATION: Synthetic

<400> SEQUENCE: 38
ccatcctcta gaccgccatg aagacagtga ctggaccttt g                  41

<210> SEQ ID NO 39
<211> LENGTH: 50
<212> TYPE: DNA
<213> ORGANISM: Artificial Sequence
<220> FEATURE:
```

<223> OTHER INFORMATION: Synthetic

<400> SEQUENCE: 39
tggtggctcc ggatccggac cgcttggccc gactggacca cagcctcagc          50

<210> SEQ ID NO 40
<211> LENGTH: 51
<212> TYPE: DNA
<213> ORGANISM: Artificial Sequence
<220> FEATURE:
<223> OTHER INFORMATION: Synthetic

<400> SEQUENCE: 40
gtaccgtcga ctgcagaatt cggtcaggaa ttttttttct tgaccatggc c         51

<210> SEQ ID NO 41
<211> LENGTH: 51
<212> TYPE: DNA
<213> ORGANISM: Artificial Sequence
<220> FEATURE:
<223> OTHER INFORMATION: Synthetic

<400> SEQUENCE: 41
gggccaagcg gtccggatcc ggagccacca acttcagcct gctgaagcag g         51

<210> SEQ ID NO 42
<211> LENGTH: 52
<212> TYPE: DNA
<213> ORGANISM: Artificial Sequence
<220> FEATURE:
<223> OTHER INFORMATION: Synthetic

<400> SEQUENCE: 42
accaacttca gcctgctgaa gcaggccggc gacgtggagg agaaccccgg cc        52

<210> SEQ ID NO 43
<211> LENGTH: 44
<212> TYPE: DNA
<213> ORGANISM: Artificial Sequence
<220> FEATURE:
<223> OTHER INFORMATION: Synthetic

<400> SEQUENCE: 43
tggaggagaa ccccggcccc atggctacaa ggctcctctg ttac                44

<210> SEQ ID NO 44
<211> LENGTH: 6
<212> TYPE: PRT
<213> ORGANISM: Homo sapiens

<400> SEQUENCE: 44

Asn Ser Ala Ser Gln Ser
1               5

<210> SEQ ID NO 45
<211> LENGTH: 6
<212> TYPE: PRT
<213> ORGANISM: Homo sapiens

<400> SEQUENCE: 45

Val Tyr Ser Ser Gly Asn
1               5

<210> SEQ ID NO 46
<211> LENGTH: 11

<212> TYPE: PRT
<213> ORGANISM: Homo sapiens

<400> SEQUENCE: 46

Val Val His Ser Ser Asn Thr Gly Lys Leu Ile
1               5                   10

<210> SEQ ID NO 47
<211> LENGTH: 5
<212> TYPE: PRT
<213> ORGANISM: Homo sapiens

<400> SEQUENCE: 47

Met Asn His Glu Tyr
1               5

<210> SEQ ID NO 48
<211> LENGTH: 6
<212> TYPE: PRT
<213> ORGANISM: Homo sapiens

<400> SEQUENCE: 48

Ser Val Gly Ala Gly Ile
1               5

<210> SEQ ID NO 49
<211> LENGTH: 18
<212> TYPE: PRT
<213> ORGANISM: Homo sapiens

<400> SEQUENCE: 49

Ala Ser Ser Tyr Ser Leu Thr Ser Gly Gly Ala Leu Val Ser Tyr Glu
1               5                   10                  15

Gln Tyr

<210> SEQ ID NO 50
<211> LENGTH: 121
<212> TYPE: PRT
<213> ORGANISM: Homo sapiens

<400> SEQUENCE: 50

Met Ile Ser Leu Arg Val Leu Val Ile Leu Trp Leu Gln Leu Ser
1               5                   10                  15

Trp Val Trp Ser Gln Arg Lys Glu Val Glu Gln Asp Pro Gly Pro Phe
                20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
        50                  55                  60

Pro Lys Leu Leu Met Ser Val Tyr Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val His
            100                 105                 110

Ser Ser Asn Thr Gly Lys Leu Ile Phe
        115                 120

<210> SEQ ID NO 51
<211> LENGTH: 129
<212> TYPE: PRT

<213> ORGANISM: Homo sapiens

<400> SEQUENCE: 51

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Leu Thr Ser Gly Gly Ala Leu Val Ser Tyr Glu Gln Tyr
        115                 120                 125

Phe

<210> SEQ ID NO 52
<211> LENGTH: 159
<212> TYPE: PRT
<213> ORGANISM: Homo sapiens

<400> SEQUENCE: 52

Gly Gln Gly Thr Thr Leu Gln Val Lys Pro Asp Ile Gln Asn Pro Asp
1               5                   10                  15

Pro Ala Val Tyr Gln Leu Arg Asp Ser Lys Ser Ser Asp Lys Ser Val
            20                  25                  30

Cys Leu Phe Thr Asp Phe Asp Ser Gln Thr Asn Val Ser Gln Ser Lys
        35                  40                  45

Asp Ser Asp Val Tyr Ile Thr Asp Lys Thr Val Leu Asp Met Arg Ser
    50                  55                  60

Met Asp Phe Lys Ser Asn Ser Ala Val Ala Trp Ser Asn Lys Ser Asp
65                  70                  75                  80

Phe Ala Cys Ala Asn Ala Phe Asn Asn Ser Ile Ile Pro Glu Asp Thr
                85                  90                  95

Phe Phe Pro Ser Pro Glu Ser Ser Cys Asp Val Lys Leu Val Glu Lys
            100                 105                 110

Ser Phe Glu Thr Asp Thr Asn Leu Asn Phe Gln Asn Leu Ser Val Ile
        115                 120                 125

Gly Phe Arg Ile Leu Leu Leu Lys Val Ala Gly Phe Asn Leu Leu Met
    130                 135                 140

Thr Leu Arg Leu Trp Ser Ser Arg Ala Lys Arg Ser Gly Ser Gly
145                 150                 155

<210> SEQ ID NO 53
<211> LENGTH: 188
<212> TYPE: PRT
<213> ORGANISM: Homo sapiens

<400> SEQUENCE: 53

Gly Pro Gly Thr Arg Leu Thr Val Thr Glu Asp Leu Lys Asn Val Phe
1               5                   10                  15

-continued

Pro Pro Glu Val Ala Val Phe Glu Pro Ser Glu Ala Glu Ile Ser His
            20                  25                  30

Thr Gln Lys Ala Thr Leu Val Cys Leu Ala Thr Gly Phe Tyr Pro Asp
        35                  40                  45

His Val Glu Leu Ser Trp Trp Val Asn Gly Lys Glu Val His Ser Gly
    50                  55                  60

Val Ser Thr Asp Pro Gln Pro Leu Lys Glu Gln Pro Ala Leu Asn Asp
65                  70                  75                  80

Ser Arg Tyr Cys Leu Ser Ser Arg Leu Arg Val Ser Ala Thr Phe Trp
                85                  90                  95

Gln Asn Pro Arg Asn His Phe Arg Cys Gln Val Gln Phe Tyr Gly Leu
            100                 105                 110

Ser Glu Asn Asp Glu Trp Thr Gln Asp Arg Ala Lys Pro Val Thr Gln
        115                 120                 125

Ile Val Ser Ala Glu Ala Trp Gly Arg Ala Asp Cys Gly Phe Thr Ser
130                 135                 140

Glu Ser Tyr Gln Gln Gly Val Leu Ser Ala Thr Ile Leu Tyr Glu Ile
145                 150                 155                 160

Leu Leu Gly Lys Ala Thr Leu Tyr Ala Val Leu Val Ser Ala Leu Val
                165                 170                 175

Leu Met Ala Met Val Lys Arg Lys Asp Ser Arg Gly
            180                 185

<210> SEQ ID NO 54
<211> LENGTH: 280
<212> TYPE: PRT
<213> ORGANISM: Homo sapiens

<400> SEQUENCE: 54

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val His
            100                 105                 110

Ser Ser Asn Thr Gly Lys Leu Ile Phe Gly Gln Gly Thr Thr Leu Gln
        115                 120                 125

Val Lys Pro Asp Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

```
Asn Asn Ser Ile Ile Pro Glu Asp Thr Phe Phe Pro Ser Pro Glu Ser
            210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Arg Ala Lys Arg Ser Gly Ser Gly
            275                 280

<210> SEQ ID NO 55
<211> LENGTH: 317
<212> TYPE: PRT
<213> ORGANISM: Homo sapiens

<400> SEQUENCE: 55

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Leu Thr Ser Gly Gly Ala Leu Val Ser Tyr Glu Gln Tyr
        115                 120                 125

Phe Gly Pro Gly Thr Arg Leu Thr Val Thr Glu Asp Leu Lys Asn Val
130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Tyr Pro
                165                 170                 175

Asp His Val Glu Leu Ser Trp Trp Val Asn Gly Lys Glu Val His Ser
            180                 185                 190

Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
            260                 265                 270

Ser Glu Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Ala Leu
```

|  | 290 |  | 295 |  | 300 |  |  |  |
|---|---|---|---|---|---|---|---|---|
| Val | Leu | Met | Ala | Met | Val | Lys | Arg | Lys | Asp | Ser | Arg | Gly |
| 305 |  |  |  | 310 |  |  |  | 315 |

<210> SEQ ID NO 56
<211> LENGTH: 843
<212> TYPE: DNA
<213> ORGANISM: Homo sapiens

<400> SEQUENCE: 56

```
atgatatcct tgagagtttt actggtgatc ctgtggcttc agttaagctg ggtttggagc      60
caacggaagg aggtggagca ggatcctgga cccttcaatg ttccagaggg agccactgtc     120
gctttcaact gtacttacag caacagtgct tctcagtctt tcttctggta cagacaggat     180
tgcaggaaag aacctaagtt gctgatgtcc gtatactcca gtggtaatga agatggaagg     240
tttacagcac agctcaatag agccagccag tatatttccc tgctcatcag agactccaag     300
ctcagtgatt cagccaccta cctctgtgtg gtccactcta gcaacacagg caaactaatc     360
tttgggcaag ggacaacttt acaagtaaaa ccagatatcc agaaccctga ccctgccgtg     420
taccagctga gagactctaa atccagtgac aagtctgtct gcctattcac cgattttgat     480
tctcaaacaa atgtgtcaca agtaaggat tctgatgtgt atatcacaga caaaactgtg     540
ctagacatga ggtctatgga cttcaagagc aacagtgctg tggcctggag caacaaatct     600
gactttgcat gtgcaaacgc cttcaacaac agcattattc cagaagacac cttcttcccc     660
agcccagaaa gttcctgtga tgtcaagctg gtcgagaaaa gctttgaaac agatacgaac     720
ctaaactttc aaaacctgtc agtgattggg ttccgaatcc tcctcctgaa agtggccggg     780
tttaatctgc tcatgacgct gcggctgtgg tccagccggg ccaagcggtc cggatccgga     840
tga                                                                    843
```

<210> SEQ ID NO 57
<211> LENGTH: 954
<212> TYPE: DNA
<213> ORGANISM: Homo sapiens

<400> SEQUENCE: 57

```
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagtt actctttgac tagcggggga     360
gccttagtct cctacgagca gtacttcggg ccgggcacca ggctcacggt cacagaggac     420
ctgaaaaacg tgttcccacc cgaggtcgct gtgtttgagc atcgagaagc agagatctcc     480
cacacccaaa aggccacact ggtatgcctg gccacaggct tctaccccga ccacgtggag     540
ctgagctggt gggtgaatgg gaaggaggtg cacagtgggg tcagcacaga cccgcagccc     600
ctcaaggagc agcccgccct caatgactcc agatactgcc tgagcagccg cctgagggtc     660
tcggccacct tctggcagaa ccccgcaac cacttccgct gtcaagtcca gttctacggg     720
ctctcggaga tgacgagtg gacccaggat agggccaaac ccgtcaccca gatcgtcagc     780
gccgaggcct ggggtagagc agactgtggc ttcacctccg agtcttacca gcaagggtc     840
```

-continued

```
ctgtctgcca ccatcctcta tgagatcttg ctagggaagg ccaccttgta tgccgtgctg      900
gtcagtgccc tcgtgctgat ggctatggtc aagagaaagg attccagagg ctag             954
```

<210> SEQ ID NO 58
<211> LENGTH: 9
<212> TYPE: PRT
<213> ORGANISM: Homo sapiens

<400> SEQUENCE: 58

```
Leu Val Leu Glu Ile Phe Thr Leu Leu
1               5
```

ANTI-THYROGLOBULIN T CELL RECEPTORS

CROSS-REFERENCE TO RELATED APPLICATIONS

This patent application is a U.S. national stage of PCT/US2015/060282, filed Nov. 12, 2015, which claims the benefit of U.S. Provisional Patent Application No. 62/079,713, filed Nov. 14, 2014, each of which is incorporated by reference herein in its entirety.

STATEMENT REGARDING FEDERALLY SPONSORED RESEARCH OR DEVELOPMENT

This invention was made with Government support under project number Z01BC011337-04 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 68,882 Byte ASCII (Text) file named "728417_ST25.txt,"," dated May 2, 2017.

BACKGROUND OF THE INVENTION

The incidence of thyroid cancer in the United States has been increasing over the last four decades (Davies et al., *JAMA Otolaryngol Head Neck Surg.*, 140(4): 317-322 (2014)). Despite advances in treatments such as thyroidectomy and adjuvant radioactive iodine (RAI) therapy, the prognosis for thyroid cancer, particularly advanced or metastatic thyroid cancer, may be poor. Accordingly, there exists an unmet need for additional treatments for cancer, particularly thyroid cancer.

BRIEF SUMMARY OF THE INVENTION

An embodiment of the invention provides an isolated or purified T cell receptor (TCR) having antigenic specificity for human thyroglobulin (TG) and comprising an alpha (α) chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a beta (β) chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

An embodiment of the invention provides an isolated or purified TCR having antigenic specificity for human TG and comprising an α chain CDR1 comprising the amino acid sequence of SEQ ID NO: 44, an α chain CDR2 comprising the amino acid sequence of SEQ ID NO: 45, an α chain CDR3 comprising the amino acid sequence of SEQ ID NO: 46, a β chain CDR1 comprising the amino acid sequence of SEQ ID NO: 47, a β chain CDR2 comprising the amino acid sequence of SEQ ID NO: 48, and a β chain CDR3 comprising the amino acid sequence of SEQ ID NO: 49.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting, the presence of cancer in a mammal and methods of treating or preventing cancer in a mammal are further provided by the invention.

DETAILED DESCRIPTION OF THE INVENTION

Figure 1:
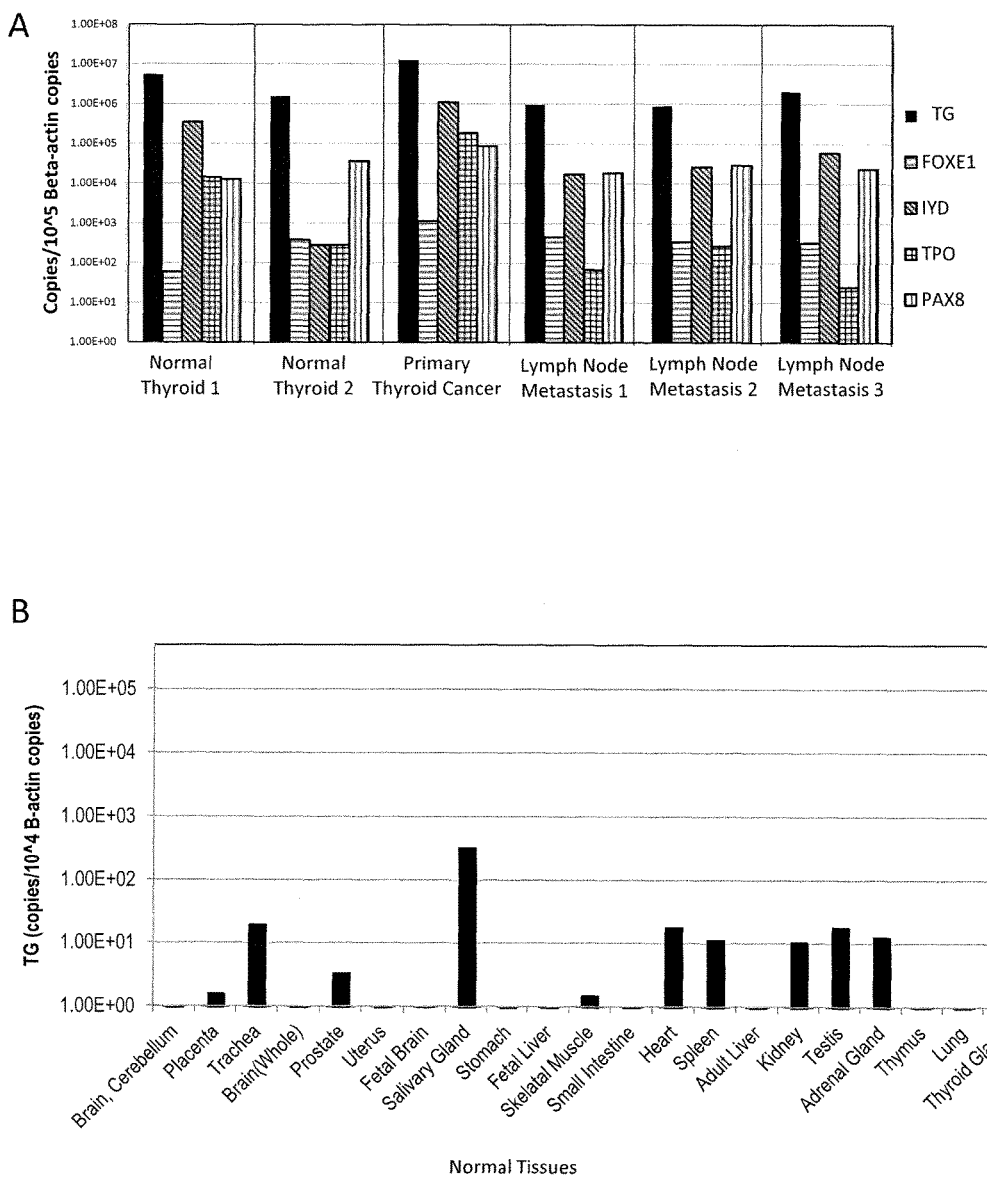
FIG. 1A is a graph showing the number of copies of TG (black bars), forkhead box E1 (FOXE1) (horizontally striped bars), iodotyrosine deiodinase (IYD) (slashed bars), thyroid peroxidase (TPO) (boxed bars), and pair box 8 (PAX8) (vertically striped bars) RNA relative to $1 \times 10^5$ ($10^5$) copies of β-actin RNA measured in two normal thyroid samples (normal thyroid 1 and 2), one primary thyroid cancer sample, and three lymph node metastasis samples (lymph node metastasis 1, 2, and 3).
FIG. 1B is a graph showing the number of copies of TG RNA relative to $1 \times 10^4$ copies of β-actin RNA measured in various normal tissue samples.

An embodiment of the invention provides an isolated or purified TCR having antigenic specificity for human TG.

The inventive TCR (including functional portions and functional variants thereof) may have antigenic specificity for any human TG protein, polypeptide or peptide. In an embodiment of the invention, the TCR (including functional portions and functional variants thereof) has antigenic specificity for a human TG protein comprising or consisting of the amino acid sequence of SEQ ID NO: 1. In an embodiment of the invention, the TCR (including functional portions and functional variants thereof) has antigenic specificity for a human $TG_{470-478}$ peptide comprising or consisting of the amino acid sequence of NLFGGKFLV (SEQ ID NO: 2) or a human $TG_{3-11}$ peptide comprising or consisting of the amino acid sequence of LVLEIFTLL (SEQ ID NO: 58). In a preferred embodiment of the invention, the TCR (including functional portions and functional variants thereof) has antigenic specificity for a human $TG_{470-478}$ peptide comprising or consisting of the amino acid sequence of NLFGGKFLV (SEQ ID NO: 2).

In an embodiment of the invention, the inventive TCRs (including functional portions and functional variants thereof) are able to recognize human TG in a major histocompatibility complex (MHC) class 1-dependent manner. "MHC class I-dependent manner," as used herein, means that the TCR (including functional portions and functional variants thereof) elicits an immune response upon binding to TG within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The TCRs (including functional portions and functional variants thereof) of the invention provide many advantages, including when expressed by cells used for adoptive cell transfer. TG has a high level of expression that is limited to differentiated thyroid cancer and normal thyroid, a dispensable tissue that may have already been removed in thyroid cancer patients. TG is also expressed in neuroblastoma. Without being bound to a particular theory or mechanism, it is believed that the inventive TCRs (including functional portions and functional variants thereof) advantageously target the destruction of cancer cells while minimizing or eliminating the destruction of normal, non-cancerous, non-thyroid cells, thereby reducing, for example, by minimizing or eliminating, toxicity. Moreover, the inventive TCRs (including functional portions and functional variants thereof) may, advantageously, successfully treat or prevent TG-positive cancers that do not respond to other types of treatment such as, for example, chemotherapy, surgery, or radiation. Additionally, the inventive TCRs (including functional portions and functional variants thereof) provide highly avid recognition of TG, which may, advantageously, provide the ability to recognize unmanipulated tumor cells (e.g., tumor cells that have not been treated with interferon (IFN)-γ, transfected with a vector encoding one or both of TG and HLA-A2, pulsed with the $TG_{470-478}$ peptide, or a combination thereof).

The phrase "antigenic specificity," as used herein, means that the TCR (including functional portions and functional variants thereof) can specifically bind to and immunologically recognize TG with high avidity. For example, a TCR (including functional portions and functional variants thereof) may be considered to have "antigenic specificity" for TG if T cells expressing the TCR (or functional portion or functional variant thereof) secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative HLA-A2$^+$ target cells pulsed with a low concentration of TG peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) HLA-A2$^+$ target cells into which a nucleotide sequence encoding TG has been introduced such that the target cell expresses TG. Cells expressing the inventive TCRs (including functional portions and functional variants thereof) may also secrete IFN-γ upon co-culture with antigen-negative HLA-A2$^+$ target cells pulsed with higher concentrations of TG peptide.

Alternatively or additionally, a TCR (including functional portions and functional variants thereof) may be considered to have "antigenic specificity" for TG if T cells expressing the TCR (or functional portion or functional variant thereof) secrete at least twice as much IFN-γ upon co-culture with (a) antigen-negative HLA-A2$^+$ target cells pulsed with a low concentration of TG peptide or (b) HLA-A2$^+$ target cells into which a nucleotide sequence encoding TG has been introduced such that the target cell expresses TG as compared to the amount of IFN-γ expressed by a negative control. The negative control may be, for example, (i) T cells expressing the TCR (or a functional portion or functional variant thereof), co-cultured with (a) antigen-negative HLA-A2$^+$ target cells pulsed with the same concentration of an irrelevant peptide (e.g., some other peptide with a different sequence from the TG peptide) or (b) HLA-A2$^+$ target cells into which a nucleotide sequence encoding an irrelevant peptide has been introduced such that the target cell expresses the irrelevant peptide, or (ii) untransduced T cells (e.g., derived from PBMC, which do not express the TCR, or a functional portion or functional variant thereof) co-cultured with (a) antigen-negative HLA-A2$^+$ target cells pulsed with the same concentration of TG peptide or (b) HLA-A2$^+$ target cells into which a nucleotide sequence encoding TG has been introduced such that the target cell expresses TG. IFN-γ secretion may be measured by methods known in the art such as, for example, enzyme-linked immunosorbent assay (ELISA).

Alternatively or additionally, a TCR (including functional portions and functional variants thereof), may be considered to have "antigenic specificity" for TG if at least twice as many of the numbers of T cells expressing the TCR (or the functional portion or functional variant thereof), secrete IFN-γ upon co-culture with (a) antigen-negative HLA-A2$^+$ target cells pulsed with a low concentration of TG peptide or (b) HLA-A2$^+$ target cells into which a nucleotide sequence encoding TG has been introduced such that the target cell expresses TG as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for TG.

In an embodiment of the invention, the TCR comprises two polypeptide chains, each of which comprises a variable region comprising a complementarity determining region (CDR) 1, a CDR2, and a CDR3 of a TCR. In an embodiment of the invention, the TCR comprises a first polypeptide chain comprising a CDR1 comprising the amino acid sequence of SEQ ID NO: 3 or 44 (CDR1 of α chain), a CDR2 comprising the amino acid sequence of SEQ ID NO: 4 or 45 (CDR2 of α chain), and a CDR3 comprising the amino acid sequence of SEQ ID NO: 5 or 46 (CDR3 of α chain), and a second polypeptide chain comprising a CDR1 comprising the amino acid sequence of SEQ ID NO: 6 or 47 (CDR1 of β chain), a CDR2 comprising the amino acid sequence of SEQ ID NO: 7 or 48 (CDR2 of β chain), and a CDR3 comprising the amino acid sequence of SEQ ID NO: 8 or 49 (CDR3 of β chain). In this regard, the inventive TCR can comprise any one or more of the amino acid sequences selected from the group consisting of SEQ ID NOs: 3-8 or SEQ ID NOs: 44-49. Preferably, the TCR comprises the amino acid sequences of SEQ ID NOs: 3-5, SEQ ID NOs: 6-8, SEQ ID NOs: 44-46, or SEQ ID NOs: 47-49. In an especially preferred embodiment, the TCR comprises the amino acid sequences of all of SEQ ID NOs: 3-8 or all of SEQ ID NOs: 44-49.

In an embodiment of the invention, the TCR comprises an amino acid sequence of a variable region of a TCR comprising the CDRs set forth above. In this regard, the TCR can comprise the amino acid sequence of SEQ ID NO: 9 or 50 (variable region of α chain); SEQ ID NO: 10 or 51 (variable region of β chain); both SEQ ID NOs: 9 and 10; or both SEQ ID NOs: 50 and 51. Preferably, the inventive TCR comprises the amino acid sequences of both SEQ ID NOs: 9 and 10 or both SEQ ID NOs: 50 and 51.

In an embodiment of the invention, the TCR further comprises an amino acid sequence of a constant region of a TCR. In this regard, the TCR can comprise the amino acid sequence of SEQ ID NO: 13 or 52 (constant region of α chain), SEQ ID NO: 14 or 53 (constant region of β chain), both SEQ ID NOs: 13 and 14, or both SEQ ID NOs: 52 and 53. Preferably, the inventive TCR comprises the amino acid sequences of both SEQ ID NOs: 13 and 14 or both SEQ ID NOs: 52 and 53.

In an embodiment of the invention, the inventive TCR may comprise a combination of a variable region and a constant region. In this regard, the TCR can comprise an α chain comprising the amino acid sequences of both SEQ ID NO: 9 (variable region of α chain) and SEQ ID NO: 13 (constant region of α chain); a β chain comprising the amino acid sequences of both SEQ ID NO: 10 (variable region of β chain) and SEQ ID NO: 14 (constant region of β chain); an α chain comprising the amino acid sequences of both SEQ ID NO: 50 (variable region of α chain) and SEQ ID NO: 52 (constant region of α chain); a β chain comprising the amino acid sequences of both SEQ ID NO: 51 (variable region of β chain) and SEQ ID NO: 53 (constant region of β chain); the amino acid sequences of all of SEQ ID NOs: 9, 10, 13, and 14; or the amino acid sequences of all of SEQ ID NOs: 50-53. Preferably, the inventive TCR comprises the amino acid sequences of all of SEQ ID NOs: 9, 10, 13, and 14 or all of SEQ ID NOs: 50-53.

In an embodiment of the invention, the inventive TCR may comprise a combination of any of the CDR regions described herein and a constant region. In this regard, the TCR can comprise an α chain comprising the amino acid sequences of all of SEQ ID NOs: 3-5 and 13; a β chain comprising the amino acid sequences of all of SEQ ID NOs: 6-8 and 14; or the amino acid sequences of all of SEQ ID NOs: 3-8 and 13-14. In an embodiment of the invention, the TCR can comprise an α chain comprising the amino acid sequences of all of SEQ ID NOs: 44-46 and 52; a β chain comprising the amino acid sequences of all of SEQ ID NOs: 47-49 and 53; or the amino acid sequences of all of SEQ ID NOs: 44-49 and 52-53.

In an embodiment of the invention, the inventive TCR can comprise an α chain of a TCR and a β chain of a TCR. Each of the α chain and β chain of the inventive TCR can independently comprise any amino acid sequence. In this regard, the α chain of the inventive TCR can comprise the amino acid sequence of SEQ ID NO: 11 or 54. An α chain of this type can be paired with any β chain of a TCR. In this regard, the β chain of the inventive TCR can comprise the amino acid sequence of SEQ ID NO: 12 or 55. The inventive TCR, therefore, can comprise the amino acid sequence of SEQ ID NO: 11, SEQ ID NO: 12, SEQ ID NO: 54, SEQ ID NO: 55, both SEQ ID NOs: 11 and 12, or both SEQ ID NOs: 54 and 55. Preferably, the inventive TCR comprises the amino acid sequences of both SEQ ID NOs: 11 and 12 or both SEQ ID NOs: 54 and 55.

In an embodiment of the invention, the TCR is a murine TCR or a human TCR. As used herein, the term "murine" or "human," when referring to a TCR or any component of a TCR described herein (e.g., complementarity determining region (CDR), variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively. In an embodiment of the invention, a TCR comprising (i) all of SEQ ID NOs: 3-8; (ii) SEQ ID NOs: 9 and 10; (iii) SEQ ID NOs: 11 and 12; (iv) all of SEQ ID NOs: 3-8 and 13-14; or (v) all of SEQ ID NOs: 9, 10, 13, and 14 is a murine TCR. In an embodiment of the invention, a TCR comprising (i) all of SEQ ID NOs: 44-49; (ii) SEQ ID NOs: 50 and 51; (iii) SEQ ID NOs: 54 and 55; (iv) all of SEQ ID NOs: 44-49 and 52-53; or (v) all of SEQ ID NOs: 50-53 is a human TCR. In an embodiment of the invention, the murine TCR (including functional portions and functional variants thereof) has antigenic specificity for a human $TG_{470-478}$ peptide comprising or consisting of the amino acid sequence of NLFGGKFLV (SEQ ID NO: 2) and the human TCR has antigenic specificity for a human $TG_{3-11}$ peptide comprising or consisting of the amino acid sequence of LVLEIFTLL (SEQ ID NO: 58).

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to TG for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gin, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 11, SEQ ID NO: 12, SEQ ID NO: 54, SEQ ID NO: 55, both SEQ ID NOs: 11 and 12, or both SEQ ID NOs: 54 and 55. Also, for instance, the inventive TCRs (including functional variants thereof), polypeptides, or proteins can consist essentially of the amino acid sequence(s) of SEQ ID NO: 9, SEQ ID NO: 10, SEQ ID NO: 50, SEQ ID NO: 51, both SEQ ID NOs: 9 and 10, or both SEQ ID NOs: 50 and 51. Furthermore, the inventive TCRs (including functional variants thereof), polypeptides, or proteins can consist essentially of the amino acid sequence of SEQ ID NO: 3 or 44 (CDR1 of α chain), SEQ ID NO: 4 or 45 (CDR2 of α chain), SEQ ID NO: 5 or 46 (CDR3 of α chain), SEQ ID NO: 6 or 47 (CDR1 of β chain), SEQ ID NO: 7 or 48 (CDR2 of β chain), SEQ ID NO: 8 or 49 (CDR3 of β chain), or any combination thereof, e.g., SEQ ID NOs: 3-5; 6-8; 3-8; 44-46; 47-49; or 44-49.

Also provided by the invention is a polypeptide comprising a functional portion of any of the TCRs (or functional variants thereof) described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to TG. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to TG (e.g., in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to TG; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3 or 44 (CDR1 of α chain), 4 or 45 (CDR2 of α chain), 5 or 46 (CDR3 of α chain), 6 or 47 (CDR1 of β chain), 7 or 48 (CDR2 of β chain), 8 or 49 (CDR3 of β chain), or a combination thereof. Preferably, the inventive polypeptide comprises a functional portion comprising the amino acid sequences of SEQ ID NOs: 3-5; 6-8; 44-46; 47-49; all of SEQ ID NOs: 3-8; or all of SEQ ID NOs: 44-49. More preferably, the polypeptide comprises a functional portion comprising the amino acid sequences of all of SEQ ID NOs: 3-8 or all of SEQ ID NOs: 44-49.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 or 50 (variable region of α chain), SEQ ID NO: 10 or 51 (variable region of β chain), both SEQ ID NOs: 9 and 10, or both SEQ ID NOs: 50 and 51. Preferably, the polypeptide comprises the amino acid sequences of both SEQ ID NOs: 9 and 10 or both SEQ ID NOs: 50 and 51.

In an embodiment of the invention, the inventive polypeptide can further comprise the constant region of the inventive TCR or functional variant thereof set forth above. In this regard, the polypeptide can comprise the amino acid sequence of SEQ ID NO: 13 or 52 (constant region of α chain), SEQ ID NO: 14 or 53 (constant region of β chain), both SEQ ID NOs: 13 and 14; or both SEQ ID NOs: 52 and 53. Preferably, the polypeptide comprises the amino acid sequences of both SEQ ID NOs: 13 and 14 or both SEQ ID NOs: 52 and 53.

In an embodiment of the invention, the inventive polypeptide may comprise a combination of a variable region and a constant region of the inventive TCR or functional variant thereof. In this regard, the polypeptide can comprise the amino acid sequences of both SEQ ID NO: 9 (variable region of α chain) and SEQ ID NO: 13 (constant region of α chain), both SEQ ID NO: 10 (variable region of β chain) and SEQ ID NO: 14 (constant region of β chain), or all of SEQ ID NOs: 9, 10, 13, and 14. In an embodiment, the polypeptide can comprise the amino acid sequences of both SEQ ID NO: 50 (variable region of α chain) and SEQ ID NO: 52 (constant region of α chain), both SEQ ID NO: 51 (variable region of β chain) and SEQ ID NO: 53 (constant region of β chain), or all of SEQ ID NOs: 50-53. Preferably, the polypeptide comprises the amino acid sequences of all of SEQ ID NOs: 9, 10, 13, and 14 or all of SEQ ID NOs: 50-53.

In an embodiment of the invention, the inventive polypeptide may comprise a combination of any of the CDR regions described herein and a constant region of the inventive TCR or functional variant thereof. In this regard, the polypeptide can comprise the amino acid sequences of all of SEQ ID NOs: 3-5 and 13, all of SEQ ID NOs: 6-8 and 14, or all of SEQ ID NOs: 3-8 and 13-14. In an embodiment of the invention, the polypeptide can comprise the amino acid sequences of all of SEQ ID NOs: 44-46 and 52, all of SEQ ID NOs: 47-49 and 53, or all of SEQ ID NOs: 44-49 and 52-53. Preferably, the polypeptide comprises the amino acid sequences of all of SEQ ID NOs: 3-8 and 13-14 or all of SEQ ID NOs: 44-49 and 52-53.

In an embodiment of the invention, the inventive polypeptide can comprise the entire length of an α or β chain of the TCR or functional variant thereof described herein. In this regard, the inventive polypeptide can comprise the amino acid sequence of SEQ ID NO: 11, SEQ ID NO: 12, SEQ ID NO: 54, SEQ ID NO: 55, both SEQ ID NOs: 11 and 12, or both SEQ ID NO: 54 and 55. Preferably, the polypeptide comprises the amino acid sequences of both SEQ ID NOs: 11 and 12 or both SEQ ID NOs: 54 and 55.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 or SEQ ID NOs: 44-46 and a second polypeptide chain comprising the amino acid sequence of SEQ ID NOs: 6-8 or SEQ ID NOs: 47-49. Alternatively or additionally, the protein of the invention can comprise a first polypeptide chain comprising the amino acid sequence of SEQ ID NO: 9 or 50 and a second polypeptide chain comprising the amino acid sequence of SEQ ID NO: 10 or 51. The protein can, for example, comprise a first polypeptide chain comprising (i) the amino acid sequences of both SEQ ID NOs: 9 and 13 or all of SEQ ID NOs: 3-5 and 13 and a second polypeptide chain comprising the amino acid sequences of both SEQ ID NOs: 10 and 14 or all of SEQ ID NOs: 6-8 and 14 or (ii) the amino acid sequences of both SEQ ID NOs: 50 and 52 or all of SEQ ID NOs: 44-46 and 52 and a second polypeptide chain comprising the amino acid sequences of both SEQ ID NOs: 51 and 53 or all of SEQ ID NOs: 47-49 and 53. Alternatively or additionally, the protein of the invention can comprise a first polypeptide chain comprising the amino acid sequence of SEQ ID NO: 11 or 54 and a second polypeptide chain comprising the amino acid sequence of SEQ ID NO: 12 or 55. In this instance, the protein of the invention can be a TCR. Alternatively, if, for example, the protein comprises a single polypeptide chain comprising the amino acid sequences of both SEQ ID NOs: 11 and 12, both SEQ ID NOs: 54 and 55, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising both SEQ ID NOs: 11 and 12, both SEQ ID NOs: 54 and 55, both SEQ ID NO: 9 and 10, both SEQ ID NOs: 50 and 51, all of SEQ ID NOs; 3-8, all of SEQ ID NOs: 44-49, all of SEQ ID NOs: 9, 10, 13, and 14, all of SEQ ID NOs: 50-53, all of SEQ ID NOs: 3-8 and 13-14, or all of SEQ ID NOs: 44-49 and 52-53 may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. In an embodiment of the invention, the TCR (or functional portion or variant thereof), polypeptide, or protein comprises a self-cleaving, viral linker peptide. For example, the linker peptide may comprise SEQ ID NO: 28. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to TG; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N.Y. (2012). Alternatively, the TCRs, polypeptides, and/or proteins described herein (including functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs (including functional portions and functional variants thereof), polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, I-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs (including functional portions and functional variants thereof), polypeptides, or proteins described herein. In an embodiment of the invention, the nucleic acid may comprise the nucleotide sequence of SEQ ID NO: 22 (CDR1 of α chain); the nucleotide sequence of SEQ ID NO: 23 (CDR2 of α chain); the nucleotide sequence of SEQ ID NO: 24 (CDR3 of a chain); the nucleotide sequence of SEQ ID NO: 25 (CDR1 of β chain); the nucleotide sequence of SEQ ID NO: 26 (CDR2 of β chain); or the nucleotide sequence of SEQ ID NO: 27 (CDR3 of β chain). Preferably, the nucleic acid comprises the nucleotide sequences of all of SEQ ID NOs: 22-24; all of SEQ ID NOs: 25-27; or all of SEQ ID NOs: 22-27. In an especially preferred embodiment, the nucleic acid comprises the nucleotide sequences of all of SEQ ID NOs: 22-27. In an embodiment of the invention, the nucleic acid may comprise the nucleotide sequence of SEQ ID NO: 15 (variable region α chain); SEQ ID NO: 16 (variable region β chain); or both SEQ ID NOs: 15 and 16. Preferably, the nucleic acid comprises the nucleotide sequences of both SEQ ID NOs: 15 and 16. In another embodiment of the invention, the nucleic acid may comprise the nucleotide sequence of SEQ ID NO: 17 or 56 (full-length α chain); SEQ ID NO: 18 or 57 (full length β chain); both of SEQ ID NOs: 17 and 18, or both of SEQ ID NOs: 56 and 57. Preferably, the nucleic acid comprises the nucleotide sequences of both of SEQ ID NOs: 17 and 18 or both of SEQ ID NOs: 56 and 57.

In an embodiment of the invention, the nucleic acid further comprises a nucleotide sequence that encodes the constant region of a TCR α or β chain. In this regard, any of the nucleic acids described herein may further comprise the nucleotide sequence of SEQ ID NO: 19 (constant region of α chain); SEQ ID NO: 20 (constant region of β chain); or both SEQ ID NOs: 19 and 20. Preferably, the nucleic acid comprises the nucleotide sequence of both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; or all of SEQ ID NOs: 22-27 and 19-20. In an especially preferred embodiment, the nucleic acid comprises the nucleotide sequences of all of SEQ ID NOs: 15-16 and 19-20 or all of SEQ ID NOs: 22-27 and 19-20.

In an embodiment of the invention, a nucleic acid comprising the nucleotide sequences of SEQ ID NOs: 56 and 57 encodes a human TCR. In an embodiment of the invention, a nucleic acid comprising the nucleotide sequence of all of SEQ ID NOs: 22-24; all of SEQ ID NOs: 25-27; all of SEQ ID NOs: 22-27; both SEQ ID NOs: 15 and 16; both SEQ ID NOs: 17 and 18; both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; or all of SEQ ID NOs: 22-27 and 19-20 encodes a murine TCR.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises the nucleotide sequence of SEQ ID NO: 21 (encoding a and β chains SEQ ID NOs: 11 and 12 with a linker positioned between them).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal)

into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC).

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 or 44 (CDR1 of α chain), 4 or 45 (CDR2 of α chain), 5 or 46 (CDR3 of α chain), 6 or 47 (CDR1 of β chain), 7 or 48 (CDR2 of β chain), 8 or 49 (CDR3 of β chain), SEQ ID NO: 9 or 50 (variable region of α chain), SEQ ID NO: 10 or 51 (variable region of β chain), or a combination thereof, e.g., 3-5; 44-46; 6-8; 47-49; 3-8; 44-49; 9; 10; 50; 51; 9-10 or 50-51. More preferably, the functional portion comprises the amino acid sequences of SEQ ID NOs: 3-8, SEQ ID NOs: 44-49, SEQ ID NOs: 9 and 10, or SEQ ID NOs: 50 and 51. In a preferred embodiment, the antibody, or antigen binding portion thereof, binds to an epitope which is formed by all 6 CDRs (CDR1-3 of the α chain and CDR1-3 of the β chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays.

Suitable methods of making antibodies are known in the art. For instance, standard hybridoma methods are described in, e.g., C. A. Janeway et al. (eds.), *Immunobiology*, 8$^{th}$ Ed., Garland Publishing, New York, N.Y. (2011)). Alternatively, other methods, such as EBV-hybridoma methods, methods of producing antibodies in non-human animals, and bacteriophage vector expression systems are known in the art.

Phage display can also be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual*, 4$^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra).

Methods for generating humanized antibodies are well known in the art. Antibodies can also be produced by transgenic mice that are transgenic for specific heavy and light chain immunoglobulin genes. Such methods are known in the art and described in, for example, Janeway et al.; supra.

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology. Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., human TG), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to TG or to detect, treat, or prevent cancer.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer. Without being bound to a particular theory, the inventive TCRs (and functional variants thereof) are believed to bind specifically to TG, such that the TCR (or related inventive polypeptide or protein and functional variants thereof), when expressed by a cell, is able to mediate an immune response against a target cell expressing TG. In this regard, the invention provides a method of treating or preventing cancer in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent cancer in the mammal.

An embodiment of the invention provides any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

Also provided is a method of detecting the presence of cancer in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, neuroblastoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is thyroid cancer or neuroblastoma.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

The following materials and methods were employed in Examples 1-7.

Cell Lines, Tissues, Peptides, & Antibodies

The Hurthle Carcinoma Cell line XTC (Endocrine Surgery Branch, NCI) was maintained in Dulbecco's Modified Eagle's Medium (DMEM) (Life Technologies, Carlsbad, Calif.) including 10% fetal bovine serum (FBS; Sigma, St. Louis, Mo.), 10 IU/L thyroid stimulating hormone (TSH; Sigma-Aldrich), Insulin-Transferrin-Selenium (Life Technologies). HLA-A2-expressing XTC (XTC/A2) was established by transducing XTC with retrovirus containing HLA-A*0201 (Surgery Branch, NCI). The cell lines used included: melanoma lines 624 and 938, which were generated in the Surgery Branch from resected tumors as described in Topalian et al., J. Immunol., 142(10): 3714-25 (1989). Cos 7, T2, and 293GP cell lines were obtained from Surgery Branch, NCI. Normal human primary cultures including fibroblasts (Surgery Branch, NCI) and small airway epithelial cells (Lonza, Walkersville, Md.) were used as controls in experiments and maintained in RPMI 1640 medium (Life Technologies) with 10% FBS. Control tumor lines used included: MDA231 (breast adenocarcinoma; HLA-A2$^+$), MDA468 (breast adenocarcinoma; HLA-A2$^-$), H2087 (lung carcinoma; HLA-A2$^+$), BE-3 (Barrett's esophagus-associated adenocarcinoma of the distal esophagus; HLA-A2$^+$), SK-BR3 (breast adenocarcinoma; HLA-A2$^-$), SK-OV3 (ovarian adenocarcinoma; HLA-A2$^-$) BIC (human esophageal adenocarcinoma; HLA-A2$^+$), and four renal cell carcinoma lines (HLA-A2; Surgery Branch, NCI).

All peptides (Pi Prometrics, Huntsville, Ala.) were synthesized based on an HLA-A*0201 binding algorithm. The twenty best HLA-A2 binding 9-mers and ten best 10-mers were chosen for in vitro stimulation. Peptides 1-8 represent the following epitopes of TG: 1-TLLASICWV (SEQ ID NO: 29), 2-NLFGGKFLV (SEQ ID NO: 2), 3-ELPEFLLFL (SEQ ID NO: 30), 4-ALVLEIFTL (SEQ ID NO: 31), 5-ILQRRFLAV (SEQ ID NO: 32), 6-ALLRSGPYM (SEQ ID NO: 33), 7-LVEIFTLL (SEQ ID NO: 34), 8-VQQVQCWCV (SEQ ID NO: 35).

TAQMAN Real-Time Quantitative Polymerase Chain Reaction (RT-qPCR)

RNA was collected from surgically resected tissues or purchased commercially (Clonetech, Mountain View, Calif.). Complementary DNA (cDNA) was synthesized by the high-capacity cDNA Reverse Transcription Kit or SUPERSCRIPT III First-Strand cDNA synthesis system (Life Technologies). The following RT-PCR Taqman probes for comparison of antigens were used: 3' TG (00968047_m1), TPO (Hs00374163_A1), IYD (Hs00416923_A1), FOXE1 (Hs00915085_S1), and PAX8 (Hs00247586_m1), ACTB (Hs03023880_g1) (Life Technologies). For TG, a custom-designed Taqman primer/probe was also used to evaluate low expression of TG in a normal tissue panel. Absolute copy number was calculated based on standard curves generated by using a plasmid encoding each cDNA as a reference on the 7500 FAST Real-time PCR system (Life Technologies).

Preparation of Adenovirus

Normal thyroid total RNA was purified from a surgical specimen using RNeasy mini kit (Qiagen, Valencia, Calif.) and random hexamer-primed cDNA was synthesized by the SUPERSCRIPT III First-Strand cDNA synthesis system (Life Technologies). Two short cDNA fragments ($TG_{42-2186}$ and $TG_{2172-4292}$) from the 5' half of $TG_{42-8348}$ were PCR-amplified and cloned into the pShuttle2 vector by using an In-Fusion cloning kit (Clontech). After sequence confirmation, production of TG protein was examined by transfecting the pShuttle2/TG$_{42-4292}$ plasmid into HEK 293 cells and by conducting Western blotting (antibody: sc-7836, Santa Cruz Biotechnology). From the pShuttle2/TG$_{42-4292}$ plasmid, cytomegalovirus (CMV) promoter-TG$_{42-4292}$ fragment was obtained by restriction enzyme digestion and was cloned into the pAdeno-X plasmid. This plasmid was used for amplifying recombinant adenovirus according to the manufacturer's instructions (ADENO-X expression System 1, Clontech). Amplified virus was purified by ADENO-X maxi purification kit (Clontech, Mountain View, Calif.) and the buffer was exchanged with PBS using the PD10 gel-filtration column (GE Healthcare Life Sciences, Pittsburgh, Pa.). Titer of the infectious virus was measured by ADENO-X rapid titer kit (Clontech).

Immunization of Yeti/A2 Mice

Yeti mice (Stetson et al., *J. Exp. Med.*, 198(7): 1069-76 (2003)) were crossed to HLA-A*0201 transgenic mice to generate Yeti/HLA-A*0201 (Yeti/A2). The mice were also transgenic for an IFN-γ reporter gene, yellow fluorescent protein (YFP). In the Yeti system, the expression of YFP is driven by the IFN-γ promoter. When cells in these mice produce IFN-γ, they also express YFP which can be visualized with a fluorescent microscope or detected by fluorescence-activated cell scan (FACS). One hundred million colony forming units (CFU) of recombinant adenovirus/TG$_{42-4292}$ were used to immunize Yeti/A2 (half intravenously and the other half subcutaneously at the tail base) in two-week intervals. Two weeks after the second adenoviral immunization, splenocytes were harvested, plated onto 24-well plates at a cell concentration of one million cells/well maintained in RPMI (Life Technologies) including 10% fetal bovine serum (FBS; Life Technologies), 55 μM 2-mercaptoethanol (Life Technologies), 1 mM sodium pyruvate (Life Technologies), 1× MEMnon-essential amino acids (Life Technologies), 10 pg/mL gentamicin (Life Technologies), 10 U/mL penicillin, 100 μg/mL streptomycin (Life Technologies), and 250 ng/mL amphotericin B (Life Technologies) with recombinant human interleukin (IL)-2 (30 IU/ml). Individual peptides were added at a final concentration of 1 μM. Re-stimulation at one week was carried out as detailed below. HLA-A*0201 positive, Epstein-Barr Virus transformed B lymphoblastoid T2 cells were irradiated at 100 Gy and were pulsed with each peptide at a concentration of 1 μM for two hours at room temperature. After washing three times with the culture medium, T2 cells were added to Yeti splenocytes at the approximate cell number ratio of 1 to 1. Two days after the second in vitro stimulation, yellow fluorescent protein (YFP) expression was analyzed by fluorescent microscopy (AX10, Zeiss) and flow cytometry (FACS; FACSCanto II, BD Biosciences). Cultures with YFP expression were selected for co-culture with TG-expressing targets (XTC/A2 and Cos A2 transfected to express TG) and reactivity was examined by IFN-γ secretion. RNA was purified from cultures with TG-reactivity using an RNeasy kit for the purpose of cloning T-cell receptor genes.

Generation of Retroviral Supernatant

Retroviral supernatants were generated in 293GP cells by co-transfection with the retroviral vector encoding the anti-TG-TCR and an envelope protein (RD114) using lipofectamine 2000 (Life Technologies) as described in Robbins et al., *J. Clin. Oncol.*, 29(7): 917-24 (2011). On the next day of lipofection, medium was replaced with fresh medium. The supernatant was harvested after 48 hours (h) and used to transduce anti-CD3-stimulated peripheral blood lymphocytes (PBL).

Retroviral Transduction of Anti-CD3 Stimulated PBL

All PBL were collected via leukapheresis from patients enrolled in Institutional Review Board-approved studies. Lymphocytes were cultured as described in Cohen et al., *Cancer Res.*, 66(17): 8878-86 (2006) using AIM-V media (Life Technologies) containing 5% human serum (Valley Biomedical Inc., Winchester, Va.) and IL-2 (Prometheus, San Diego Calif.) at a concentration of 300 IU/ml for PBL. PBL from allogeneic donors were stimulated with soluble anti-CD3 (OKT3, 50 ng/mL) and IL-2 (300 IU/mL) for two days before transduction was performed. After stimulation, cells were added to 24-well plates initially coated with retronectin (10 μg/mL in 400 uL of PBS; Takara Shuzo, Japan) and subsequently loaded with virus by adding the virus-containing culture supernatant and centrifugating (2000×g 32° C., 2 h). After loading the virus, stimulated PBL were added at a concentration of 5×10$^5$ cells per well and the plates were centrifuged at 1000×g for 10 minutes (min). Plates were incubated overnight at 37° C. in 5% CO$_2$ incubator. On the following day, cells were transferred to new retronectin-coated and virus-loaded 24-well plates, and the second transduction was performed. Cells were maintained at a cell density between 0.5-1×10$^6$ cells/mL. Transduction efficiency was confirmed by FACS analysis of mouse TCR-β expression in transduced PBL.

Cytokine Release Assay

Interferon (IFN)-γ release by transduced PBL was determined as previously described in Wang et al., *J. Immunol. Methods*, 366(1-2): 43-51 (2011). Briefly, retrovirally-transduced cells (1×10$^5$) were co-cultured with 5×10$^4$ target cells (XTC, XTC/A2, Cos A2, or Cos A2 transfected with TG) or control tumor cell lines for 18-22 hrs in RPMI with 10% FBS at 37° C., 5% CO$_2$. On the subsequent day, IFN-γ secretion was determined by enzyme-linked immunosorbent assay (ELISA).

Example 1

This example demonstrates that TG is expressed in normal tissues, primary thyroid cancer, and lymph node metastases.

Expression of thyroid-specific antigens, including thyroid peroxidase (TPO), paired box 8 (PAX8), forkhead box E1 (FOXE1), iodotyrosine deiodinase (IYD) and thyroglobulin (TG) (van Staveren et al., *Cancer Res.*, 67(17): 8113-20 (2007)), was investigated by TAQMAN quantitative RT-PCR. Of all of these thyroid-specific antigens, TG maintained the highest expression in normal thyroid, primary thyroid cancer, and lymph node metastases of thyroid cancer (FIG. 1A). Low expression of TG was observed in non-thyroid, normal human tissue. TG expression in thyroid tissue was higher than expression in other normal tissues (FIG. 1B). Based on these data, TG was identified as a candidate thyroid-specific target antigen for adoptive cellular therapy.

Example 2

This example demonstrates the stimulation of Yeti/A2 splenocytes with TG$_{470-478}$.

HLA-A0201-restricted murine T cells were generated by vaccinating Yeti mice that were transgenic for HLA-A0201 and an IFN-γ reporter gene (yellow fluorescent protein (YFP)) with an adenovirus encoding the 5' half of the TG gene (TG$_{42-4292}$). The mice were vaccinated with TG-containing adenovirus on day 0, followed by a second vaccination with the same adenovirus on day 14. On day 28, splenocytes were collected and stimulated in vitro with TG peptide immediately at the time of harvest, followed by a second in vitro TG peptide stimulation on day 35.

The expression of the IFN-γ reporter gene YFP by the Yeti/A2 splenocytes was measured by flow cytometry two days after the second in vitro stimulation. YFP expression in stimulated splenocytes was also evaluated by ultraviolet (UV)-microscopy after-co-culture with T2 cells pulsed with TG cognate peptide.

Figure 2:
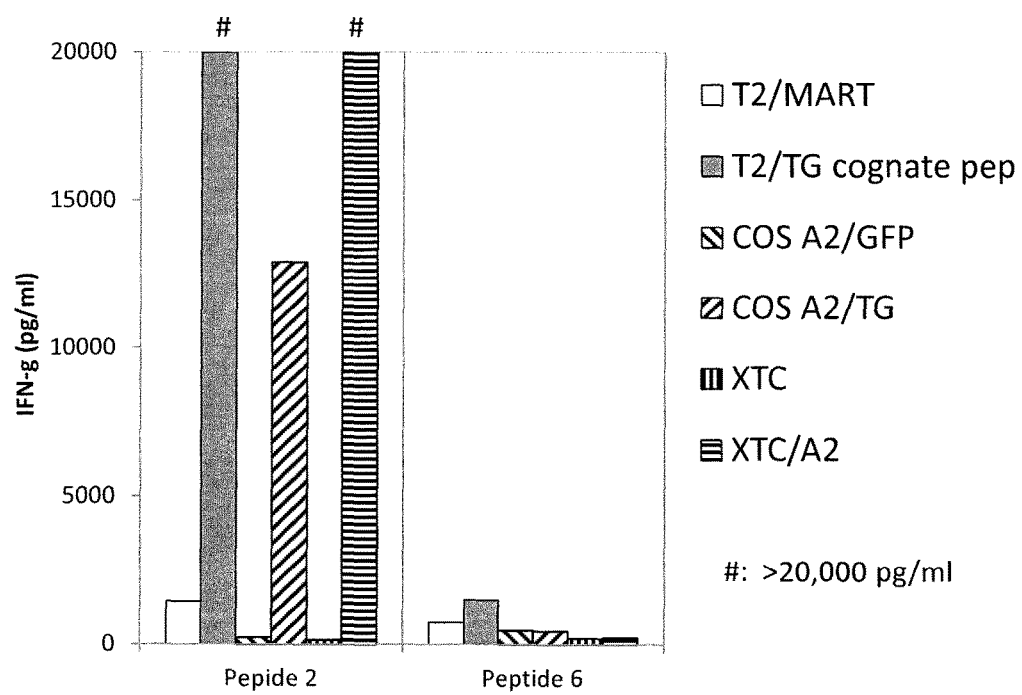
FIG. 2 is a graph showing the amount of mouse interferon (IFN)-γ (pg/ml) secreted by splenocytes from mice vaccinated with adenovirus encoding TG and stimulated twice in vitro with peptide 2 (NLFGGKFLV (SEQ ID NO: 2)) or peptide 5 (ILQRRFLAV (SEQ ID NO: 32)) when co-cultured with (identifying each bar from left to right): target T2 cells pulsed with MART-1 control peptide (T2/MART) (unshaded bars), T2 cells pulsed with TG cognate peptide (peptide 2 or 5) (grey bars), Cos 7-HLA-A*0201 cells that were transfected to express control green fluorescent protein (GFP) (Cos A2/GFP) (backslashed bars), Cos 7-HLA-A*0201 cells that were transfected to express TG (Cos A2/TG) (forward slashed bars), carcinoma cell line XTC (vertically striped bars), or XTC cells transduced to express HLA-A0201 (XTC/A2) (horizontally striped bars).

Cells that were stimulated by the peptide 2, representing the TG$_{470-478}$ epitope (NLFGGKFLV; SEQ ID NO: 2), produced a YFP signal as determined by flow cytometry and microscopy. This bulk culture was tested for reactivity against T2 cells pulsed with irrelevant (T2/MART) or the TG$_{470-478}$ peptide (T2/TG), COSA2 cells transfected with GFP or TG cDNA (Cos A2/GFP and Cos A2/TG) and XTC, TG$^+$ thyroid carcinoma cell line with or without transfection of HLA-A2. (FIG. 2). Peptide 2-stimulated splenocytes showed strong reactivity to XTC/A2 cells, Cos A2/TG cells, and T2 cells pulsed with cognate peptide.

Example 3

This example demonstrates the isolation of the murine anti-TG TCR from the TG$_{470-478}$-stimulated splenocytes of Example 2.

Total RNA was isolated from the bulk culture by an RNA isolation kit (RNeasy, Qiagen). Amplification of the 5' cDNA ends of the TCR α and β chains was done by SMARTer 5' RACE kit (Clontech) using the following primers: Universal Primer A Mix (Clonetech), α-specific primer 5'-GGCTACTTTCAGCAGGAGGA-3' (SEQ ID NO: 36), β-specific primer 5' AGGCCTCTGCACTGAT-GTTC-3' (SEQ ID NO: 37). TCR α and β cDNA molecules were then inserted into a TOPO vector by TA cloning. Plasmids from 48 individual colonies for α- and β-chains were purified and sequenced. This sequence analysis revealed oligo-clonality, with 27/48 colonies of a representing TRAV3D-3*02/J22*01, 21/48 colonies of a representing TRAV15N-1*01, and 45/47 colonies of β representing TRBV26*01/D2*01/J2-5*01. Since TRAV15N-1*01 was a nonproductive recombination, it was disregarded. Based on the sequencing data, the following primers were synthesized (Life Technologies): TCR α forward (SEQ ID NO: 38) and TCR α reverse (SEQ ID NO: 39) for the α chain and TCR β forward (SEQ ID NO: 43) and TCR β reverse (SEQ ID NO: 40) for the β chain. By RT-PCR, full length cDNA of the α chain and β chain were isolated. The α chain and β chain cDNA encoded SEQ ID NOs: 11 and 12, respectively.

Example 4

This example demonstrates the generation of a retroviral recombinant expression vector encoding the murine anti-TG TCR of Example 3.

After the isolation of the full length α chain and β chain as described in Example 3, a self-cleaving 2A peptide sequence was introduced into the 5' of β chain using a 7:2:1 molar ratio mix of SEQ ID NOs: 41, 42 and 43 as the forward primer and SEQ ID NO: 40 as the reverse primer.

After the amplification, the α-chain and 2A-β-chain were cloned into the retroviral vector, MSGV1 (SEQ ID NO: 21), which is a derivative of the murine stem cell virus-based retroviral vector pMSGV (Zhao et al., *J. Immunol.*, 174(7): 4415-23 (2005)) by the InFusion reaction (Clontech). The plasmid encoding the mouse anti-TG TCR was a 7394 base pair (bp) sequence encoding the α and β-chains (SEQ ID NOs: 11 and 12, respectively) separated by a self-cleaving p2A region (SEQ ID: NO 28). The sequence of the plasmid was confirmed by Sanger sequencing.

Example 5

This example demonstrates the transduction of donor PBL with a retroviral vector encoding the murine anti-TG TCR.

Anti-CD3 stimulated, human donor PBL were retrovirally transduced with the vector of Example 4. Three days after transduction, FACS analysis was performed by labeling the T-cells with antibodies against CD3, CD8, and the mouse TCR-β chain or MART-1/HLA-A2 tetramer. The efficiency of transduction of PBL from three donor patients was high (80-90%) without significant differences between CD4+ and CD8+ T-cells. The experiments were performed more than five times, each of which gave similar results.

Example 6

This example demonstrates the reactivity of the murine anti-TG TCR against HLA-A*0201$^+$/TG$^+$ targets.

Figure 3:
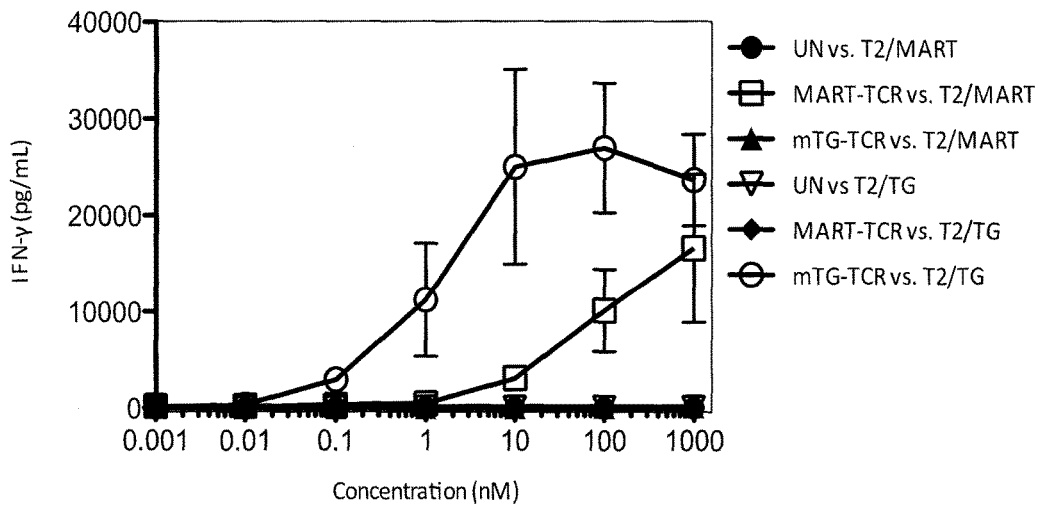
FIG. 3A is a graph showing the amount of IFN-γ (pg/ml) measured upon co-culture of effector untransduced (UN) PBL with target T2 cells pulsed with various concentrations (nM) of MART-1 peptide (closed circles) or TG peptide NLFGGKFLV (SEQ ID NO: 2) (open triangles), effector anti-MART-1 TCR-transduced PBL with target T2 cells pulsed with various concentrations of MART-1 peptide (open squares) or TG peptide NLFGGKFLV (SEQ ID NO: 2) (diamonds), or effector murine anti-TG TCR (mTG-TCR) (SEQ ID NOs: 11 and 12)-transduced PBL with target T2 cells pulsed with various concentrations of MART-1 peptide (closed triangles) or TG peptide NLFGGKFLV (SEQ ID NO: 2) (open circles).
FIG. 3B is a graph showing the amount of IFN-γ (pg/ml) measured upon co-culture of effector untransduced (UT) PBL or PBL transduced with an anti-MART-1 TCR (MART) or the murine anti-TG TCR (mTG-TCR) (SEQ ID NOs: 11 and 12) with target cells Cos A2/GFP cells (small checkered bars), Cos A2/MART cells (large checkered bars), Cos A2/TG cells (horizontally striped bars), 624Mel cells (vertically striped bars), 938Mel cells (a melanoma-derived cell line that does not express MART-1) (forward slashed bars)), XTC cells (backslashed bars), or XTC/A2 cells (boxed bars).
Figure 3:
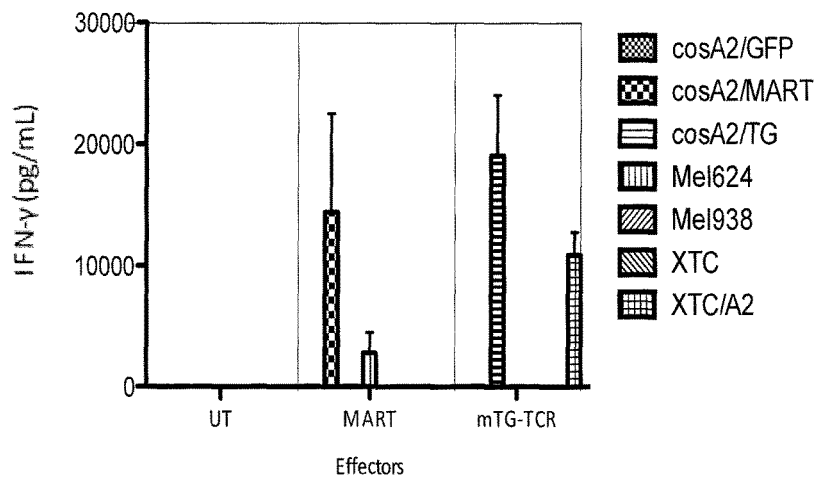

Anti-CD3 stimulated PBL were transduced with the retroviral vector encoding the murine anti-TG TCR of Example 4 or an anti-MART-1 TCR. Untransduced cells were used as a control. Three days after transduction, 1×10$^5$ transduced cells or control cells were co-cultured with 5×10$^4$ T2 cells that had been pulsed with either TG (NLFGGKFLV (SEQ ID NO: 2)) (T2/TG) or MART-1 (T2/MART-1) peptides. PBL expressing the murine anti-TG TCR (SEQ ID NOs: 11 and 12) recognized the peptide at very low concentrations (<0.1 nM), out-performing the anti-MART-1 TCR control. (FIG. 3A).

PBL transduced with a vector encoding the murine anti-TG TCR (SEQ ID NOs: 11 and 12) were analyzed for reactivity, as determined by human (h) IFN-γ release, after co-culture with tumor cell lines or cell lines transfected to express TG. High levels of IFN-γ were released by the PBL transduced with a vector encoding the murine anti-TG TCR (SEQ ID NOs: 11 and 12) in response to HLA-A2$^+$ TG$^+$ lines, including XTC/A2 and Cos A2/TG. (FIG. 3B).

Example 7

This example demonstrates the specificity of the murine anti-TG TCR for HLA-A*0201$^+$/TG$^+$ targets.

The specificity of the murine anti-TG TCR (SEQ ID NOs: 11 and 12) was tested by analyzing its reactivity against XTC, XTC/A2, and a panel of cell lines and normal tissues not expressing one or both of TG and HLA-A*0201, including H2087, BIC, BE-3, SK-OV3, SK-BR3, MDA231, MDA468, four renal cell carcinoma lines, normal human fibroblasts, and small airway epithelial epithelium cells (Table 1). As shown in Table 1, all cell lines were one or both of HLA-A*0201$^-$ and TG$^-$, except XTC/A2. The PBL transduced with a vector encoding the murine anti-TG TCR (SEQ ID NOs: 11 and 12) showed reactivity only to the HLA-A2+/TG+ XTC/A2 cell line, and showed no reactivity to any TG-negative or HLA-A*0201-negative cell lines. Further testing of the murine anti-TG TCR against TG-expressing, freshly resected, normal, primary thyroid tissues from an HLA-A*0201$^-$ patient and a HLA-A*0201$^+$ patient demonstrated that the murine anti-TG TCR transduced PBL were reactive against HLA-A*0201⁺/TG⁺, but not HLA-A*0201⁻/TG⁺ tissue by IFN-γ secretion.

TABLE 1

| Cell Line | HLA-A2+ | Tg+ |
|---|---|---|
| XTC | − | + |
| XTC/A2 | + | + |
| mel624 | + | − |
| mel938 | + | − |
| Fibroblasts | + | − |
| Small Airway Epithelial Cells | − | − |
| MDA231 | + | − |
| MDA468 | − | − |
| SK-OV3 | − | − |
| SK-BR3 | − | − |
| H2087 | + | − |
| BE-3 | + | − |
| BIC | + | − |
| RCC #1 | + | − |
| RCC #2 | + | − |
| RCC #3 | + | − |
| RCC #4 | + | − |

Example 8

This example demonstrates the isolation of a human anti-TG TCR and the transduction efficiency of the human anti-TG TCR into PBL.

Human PBL were individually stimulated four times with 30 computer algorithmically-predicted HLA-A2 high binding peptides derived from $TG_{42-4292}$. After four in vitro stimulations, $TG_{3-11}$ peptide (LVLEIFTLL, SEQ ID NO: 58)-stimulated culture showed reactivity against XTC/A2. Limiting dilution cloning was carried out for this culture and one of 28 clones analyzed, clone 14, was found to have TG-specific reactivity. After the expansion of the cells, TCR α and β genes were cloned by 5'RACE followed by RT-PCR (encoding SEQ ID NOs: 54 and 55, respectively). PBL were transduced with the retroviral expression vector encoding the human anti-TG TCR.

Transduction efficiency of human anti-TG TCR expression in transduced PBL was confirmed by FACS analysis. The efficiency of transduction of PBL from two donor patients was high (75-80%) without significant differences between CD4+ and CD8+ T-cells.

Example 9

This example demonstrates the reactivity of the human anti-TG TCR of Example 8.

PBL transduced with the human anti-TG TCR of Example 8 were co-cultured with T2 cells pulsed with various concentrations of MART-1 or $TG_{3-11}$ and IFN-γ was measured (pg/ml). The results are shown in Table 2A.

TABLE 2A

| | IFN-γ (pg/ml) | |
|---|---|---|
| Concentration of peptide pulsed | T2/MART-1 | $TG_{3-11}$ |
| 1000 nM | 73.4 | 29734.3 |
| 100 nM | 73.6 | 28600.9 |
| 10 nM | 64.7 | 16848.2 |
| 1 nM | 68.2 | 2522.1 |
| 0.1 nM | 54.5 | 325.5 |
| 0.01 nM | 89.2 | 93.2 |
| 0.001 nM | 81.8 | 72.9 |
| 0 nM | 70.3 | 75.7 |

TABLE 2A-continued

| | IFN-γ (pg/ml) | |
|---|---|---|
| Concentration of peptide pulsed | T2/MART-1 | $TG_{3-11}$ |

PBL transduced with the murine anti-TG TCR of Example 3 were co-cultured with T2 cells pulsed with various concentrations of MART-1 or $TG_{470-478}$. The results are shown in Table 2B.

TABLE 2B

| | IFN-γ (pg/ml) | |
|---|---|---|
| Concentration of peptide pulsed | T2/MART-1 | T2/$TG_{470-478}$ |
| 1000 nM | 373.7 | 47261.6 |
| 100 nM | 125.8 | 33459.2 |
| 10 nM | 50.2 | 27326.8 |
| 1 nM | 41.5 | 13124.8 |
| 0.1 nM | 36.5 | 8680 |
| 0.01 nM | 41 | 1236.8 |
| 0.001 nM | 38.2 | 136.1 |
| 0 nM | 37.7 | 55.8 |

As shown in Tables 2A and 2B, although the reactivity of the murine anti-TG TCR was superior to that of the human anti-TG TCR, PBL transduced with the human anti-TG TCR were reactive against cells pulsed with $TG_{3-11}$.

PBL transduced with the human anti-TG TCR of Example 8 or the murine anti-TG TCR of Example 3 were co-cultured with COSA2/GFP cells, COSA2/TG cells, 624Mel cells, XTC cells, or XTC/A2 cells, and IFN-γ was measured (pg/ml). The results are shown in Table 3.

TABLE 3

| | IFN-γ (pg/ml) | | | | |
|---|---|---|---|---|---|
| | COSA2/GFP | COSA2/TG | 624Mel | XTC | XTC/A2 |
| human anti-TG TCR | 15.5 | 8794.7 | 1.8 | 5.7 | 735.3 |
| murine anti-TG TCR | 19.2 | 25298.4 | 7.2 | 2.3 | 21371.9 |

As shown in Table 3, although the reactivity of the murine anti-TG TCR was superior to that of the human anti-TG TCR, PBL transduced with the human anti-TG TCR were reactive against HLA-A2+/TG+ cell lines.

In a separate experiment, PBL from two patients that were untransduced (UT) or transduced with the human anti-TG TCR of Example 8, the murine anti-TG TCR of Example 3, or an anti-MART-1 TCR were co-cultured with COSA2/GFP cells, COSA2/MART-1 cells, Cos 7-HLA-A*01 cells that were transfected to express TG (COSA1/TG cells), COSA2/TG cells, 624Mel cells (MART-1+), 938Mel cells, XTC cells, or XTC/A2 cells, and IFN-γ was measured (pg/ml). The results are shown in Table 4A (Patient 1) and Table 4B (Patient 2).

TABLE 4A

| | IFN-γ (pg/ml) | | | |
| --- | --- | --- | --- | --- |
| | UT | Anti-MART-1 TCR | human anti-TG TCR | murine anti-TG TCR |
| COSA2/GFP | 0 | 0 | 0 | 0 |
| COSA2/MART-1 | 0 | 20000 | 0 | 0 |
| COSA1/TG | 0 | 0 | 0 | 0 |
| COSA2/TG | 0 | 0 | 15500 | 20000 |
| 624Mel | 0 | 7000 | 0 | 0 |
| 938Mel | 0 | 0 | 0 | 0 |
| XTC | 0 | 0 | 0 | 0 |
| XTC/A2 | 0 | 0 | 500 | 20000 |

TABLE 4B

| | IFN-γ (pg/ml) | | | |
| --- | --- | --- | --- | --- |
| | UT | Anti-MART-1 TCR | human anti-TG TCR | murine anti-TG TCR |
| COSA2/GFP | 0 | 0 | 0 | 0 |
| COSA2/MART-1 | 0 | 20000 | 0 | 0 |
| COSA1/TG | 0 | 0 | 0 | 0 |
| COSA2/TG | 0 | 0 | 14800 | 20000 |
| 624Mel | 0 | 3800 | 0 | 0 |
| 938Mel | 0 | 0 | 0 | 0 |
| XTC | 0 | 0 | 0 | 0 |
| XTC/A2 | 0 | 0 | 300 | 17900 |

Further testing of the human anti-TG-TCR against TG-expressing, freshly resected, normal, primary thyroid tissues from an HLA-A*0201⁻ patient and a HLA-A*0201⁺ patient demonstrated that the human anti-TG-TCR transduced PBL were reactive against HLA-A*0201⁺/TG⁺, but not HLA-A*0201⁻/TG⁺ tissue, as measured by IFN-γ secretion.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T cell receptor (TCR) having antigenic specificity for the amino acid sequence of SEQ ID NO: 2 and comprising an α chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

2. The isolated or purified TCR of claim 1, comprising an α chain variable region comprising the amino acid sequence of SEQ ID NO: 9 and a β chain variable region comprising the amino acid sequence of SEQ ID NO: 10.

3. The isolated or purified TCR of claim 1, further comprising an α chain constant region comprising the amino acid sequence of SEQ ID NO: 13 and a β chain constant region comprising the amino acid sequence of SEQ ID NO: 14.

4. The isolated or purified TCR of claim 1, comprising an α chain comprising the amino acid sequence of SEQ ID NO: 11 and a β chain comprising the amino acid sequence of SEQ ID NO: 12.

5. The isolated or purified TCR of claim 1, comprising a self-cleaving, viral linker peptide.

6. An isolated or purified polypeptide comprising a functional portion of the TCR of claim 1, wherein the functional portion comprises the amino acid sequences of SEQ ID NOs: 3-8.

7. The isolated or purified polypeptide of claim 6, comprising a self-cleaving, viral linker peptide.

8. An isolated or purified protein comprising at least one of the polypeptides of claim 6.

9. An isolated or purified polypeptide comprising a functional portion of the TCR of claim 1, wherein the functional portion comprises the amino acid sequence of both SEQ ID NOs: 9 and 10.

10. An isolated or purified polypeptide comprising a functional portion of the TCR of claim 1, wherein the functional portion comprises the amino acid sequence of both SEQ ID NOs: 11 and 12.

11. A pharmaceutical composition comprising the TCR according to claim 1 and a pharmaceutically acceptable carrier.

12. An isolated or purified protein comprising a first polypeptide chain comprising the amino acid sequences of SEQ ID NOs: 3-5 and a second polypeptide chain comprising the amino acid sequences of SEQ ID NOs: 6-8.

13. The isolated or purified protein according to claim 12, comprising a first polypeptide chain comprising the amino acid sequence of SEQ ID NO: 9 and a second polypeptide chain comprising the amino acid sequence of SEQ ID NO: 10.

14. The isolated or purified protein according to claim 12, comprising a first polypeptide chain comprising the amino acid sequence of SEQ ID NO: 11 and a second polypeptide chain comprising the amino acid sequence of SEQ ID NO: 12.

15. The isolated or purified protein according to claim 12, wherein the protein is a fusion protein.

16. The isolated or purified protein according to claim 12, wherein the protein is a recombinant antibody.

17. The isolated or purified protein according to claim 12, comprising a self-cleaving, viral linker peptide.

18. An isolated or purified nucleic acid comprising a nucleotide sequence encoding the TCR according to claim 1.

19. The nucleic acid according to claim 18, comprising the nucleotide sequences of SEQ ID NOs: 22-27.

20. The nucleic acid according to claim 18, comprising the nucleotide sequences of SEQ ID NOs: 15 and 16.

21. The nucleic acid according to claim 18, further comprising the nucleotide sequences of SEQ ID NOs: 19 and 20.

22. The nucleic acid according to claim 18, comprising the nucleotide sequences of SEQ ID NOs: 17 and 18.

23. A recombinant expression vector comprising the nucleic acid according to claim 18.

24. The recombinant expression vector according to claim 23 comprising the nucleotide sequence of SEQ ID NO: 21.

25. An isolated host cell comprising the recombinant expression vector of claim 23.

26. The host cell according to claim 25, wherein the cell is human.

27. A population of cells comprising at least one host cell of claim 25.

* * * * *